(12) United States Patent
Ritzeler et al.

(10) Patent No.: US 7,026,331 B2
(45) Date of Patent: Apr. 11, 2006

(54) SUBSTITUTED BETA-CARBOLINES

(75) Inventors: Olaf Ritzeler, Frankfurt am Main (DE); Alfredo Castro, Winchester, MA (US); Louis Grenier, Medford, MA (US); Francois Soucy, Medford, MA (US); Wayne W. Hancock, Medfield, MA (US); Hormoz Mazdiyasni, Douglas, MA (US); Vito Palombella, Needham, MA (US); Julian Adams, Chestnut Hill, MA (US)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 10/627,978

(22) Filed: Jul. 28, 2003

(65) Prior Publication Data
US 2004/0110759 A1 Jun. 10, 2004

Related U.S. Application Data

(63) Continuation of application No. 09/812,785, filed on Mar. 15, 2001, now Pat. No. 6,627,637.

(30) Foreign Application Priority Data

| Mar. 15, 2000 | (EP) | .................................. 00105514 |
| Nov. 18, 2000 | (EP) | .................................. 00125169 |

(51) Int. Cl.
*C07D 471/02* (2006.01)
*A61K 31/44* (2006.01)

(52) U.S. Cl. ...................... 514/292; 546/81; 514/232.8; 544/126

(58) Field of Classification Search .................. 546/81; 514/292, 232.8; 544/126
See application file for complete search history.

(56) References Cited

U.S. PATENT DOCUMENTS

| 4,631,149 A |  | 12/1986 | Rinehart, Jr. et al. ........ 540/546 |
| 4,731,358 A | * | 3/1988 | Huth et al. .................... 514/81 |
| 5,532,261 A | * | 7/1996 | DiNinno et al. ........ 514/210.14 |
| 5,604,236 A |  | 2/1997 | Jakubowski et al. ......... 514/292 |
| 5,854,003 A |  | 12/1998 | Rothe et al. .................. 435/7.8 |
| 6,627,637 B1 |  | 9/2003 | Ritzeler et al. |

FOREIGN PATENT DOCUMENTS

| DE | 568 675 C | 1/1933 |
| DE | 198 07 993 A1 | 9/1999 |
| EP | 0 110 814 A2 | 6/1984 |
| EP | 0 133 000 A2 | 2/1985 |
| EP | 0 667 347 A1 | 8/1995 |
| EP | 1 048 666 A1 | 11/2000 |

OTHER PUBLICATIONS

Hagen et al, Journal of Medicinal Chemistry, vol. 30, pp. 750-753, 1987.*
Agarwal et al, Med Chemi Res, vol. 3, pp. 523-530, 1994.*
K. Smith et al., "A New Method for Bromination of Carbazoles, β-Carbolines and Iminodibenzyls by Use of N-Bromosuccinimide and Silica Gel," Tetrahedron, vol. 48, No. 36, pp. 7479-7488 (1992).
Chemical Abstract, vol. 121, No. 7, XP-002165154, Columbus, Ohio (Aug. 15, 1994).
Chemical Abstract, vol. 122, No. 19, XP-002165155, Columbus, Ohio (May 8, 1995).
Chemical Abstract, vol. 121, No. 3, XP-002165156, Columbus, Ohio (Jul. 18, 1994).
Chemical Abstract, vol. 106, No. 23, XP-002165157, Columbus, Ohio (Jun. 8, 1987).
Chemical Abstract, vol. 74, No. 1, XP-002165158, Columbus, Ohio (Jan. 4, 1971).
Chemical Abstract, vol. 92, No. 25, XP-002165159, Columbus, Ohio (Jun. 23, 1980).
C. Coulthard et al., "XCVI. The Chemotherapy of Derivatives of Harmine and Harmaline I," Biochemical Journal, Portland Press, vol. 27, No. 3, pp. 727-739, XP-000917474, ISSN: 0264-6021 (1933).
R. Konowalowa et al., "Untersuchungen in der Reihe des Harmins und Harmalins. 2.Mitteilung[1]): Nitro=und Aminoderivate des Harmins und Harmalins, O=Alkyläther des Harmols und Harmalols," vol. 273, pp. 156-163 (Nov. 1934) XP000917794.
6001 Chemical Abstract, vol. 96, No. 9, XP-002170075, Columbus, Ohio (Mar. 1, 1982).
Database RTECS 'Online, RTECS No. UU9354600, XP-002170076, Abstract (Jul. 1986).
A. Agarwal et al., "Structure-Antifilarial Activity Relationship of 5/6/7/8-Mono- or Disubstituted 1H/1-Phenyl-9 H-pyridol[3,4-b]indoles—A New Class of Potential Filaricides," Natur. Section C, vol. 49, No. 7/8, pp. 526-529 (1994).

* cited by examiner

*Primary Examiner*—Zinna Northington Davis
(74) *Attorney, Agent, or Firm*—Finnegan, Henderson, Farabow, Garrett & Dunner, L.L.P.

(57) ABSTRACT

The subject matter of the present invention is directed to novel substituted beta-carbolines, and specifically compounds of the formula I,

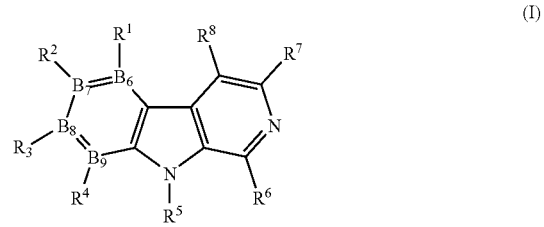

(I)

which are suitable for the production of pharmaceuticals for the prophylaxis and therapy of disorders in whose course an increased activity of IκB kinase is involved.

14 Claims, No Drawings

SUBSTITUTED BETA-CARBOLINES

This application claims benefit of priority to EP Application no. 00105514.4, filed Mar. 15, 2000, and EP Application no. 00125169.3, filed Nov. 18, 2000, both of which are incorporated herein by reference.

The present invention relates to novel substituted beta-carbolines, a process for their preparation and use thereof as pharmaceuticals.

Art related to the present invention includes U.S. Pat. Nos. 4,631,149 and 5,604,236. U.S. Pat. No. 4,631,149 discloses beta-carbolines useful as antiviral, antibacterial and antitumor agents. U.S. Pat. No. 5,604,236 discloses beta-carboline derivatives containing an acidic group, useful as thromboxane syntheses inhibitors.

NFkB is a heterodimeric transcription factor which can activate a large number of genes which code, inter alia, for proinflammatory cytokines such as IL-1, IL-2, TNFα or IL-6. NFkB is present in the cytosol of cells, building a complex with its naturally occurring inhibitor IkB. The stimulation of cells, for example by cytokines, leads to the phosphorylation and subsequent proteolytic degradation of IkB. This proteolytic degradation leads to the activation of NFkB, which subsequently migrates into the nucleus of the cell and there activates a large number of proinflammatory genes.

In disorders such as rheumatoid arthritis (in the case of inflammation), osteoarthritis, asthma, cardiac infarct, Alzheimer's disease or atherosclerosis, NFkB is activated beyond the normal extent. Inhibition of NFkB is also of benefit in cancer therapy, since it is employed there for the reinforcement of the cytostatic therapy. It has been shown that pharmaceuticals such as glucocorticoids, salicylates or gold salts, which are employed in rheumatic therapy, intervene in an inhibitory manner at various points in the NFkB-activating signal chain or interfere directly with the transcription of the genes.

The first step in the signal cascade mentioned is the degradation of IkB. This phosphorylation is regulated by the specific IkB kinase. To date, no inhibitors are known which specifically inhibit IkB kinase.

In the attempt to obtain active compounds for the treatment of rheumatoid arthritis (in the case of inflammation), osteoarthritis, asthma, cardiac infarct, Alzheimer's disease, carcinomatous disorders (potentiation of cytotoxic therapies) or atherosclerosis, the inventors have surprisingly discovered that the benzimidazoles of the present invention are strong and very specific inhibitors of IkB kinase.

The invention therefore relates to the compounds of the formula I

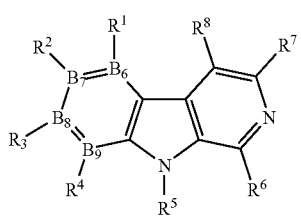

(I)

and/or a stereoisomeric form of the compounds of the formula I and/or a physiologically tolerable salt of the compounds of the formula I, where $B_6$, $B_7$, $B_8$ and $B_9$ are independently selected from the group consisting of carbon atom and nitrogen atom, where $B_6$, $B_7$, $B_8$ and $B_9$ together comprise no more than two nitrogen atoms; wherein in case a)
the substituents $R^1$, $R^2$ and $R^3$ may be independently chosen from:
1.1. hydrogen atom,
1.2. halogen,
1.3. —CN,
1.4. —COOH,
1.5. —NO$_2$,
1.6. —NH$_2$,
1.7. —O—(C$_1$–C$_{10}$)-alkyl, wherein alkyl is unsubstituted or mono- to penta-substituted by substituents independently chosen from:
   1.7.1 phenyl, which is unsubstituted or mono- to penta-substituted by substituents independently chosen from halogen or —O—(C$_1$–C$_4$)-alkyl,
   1.7.2 halogen,
   1.7.3 —NH$_2$,
   1.7.4 —OH,
   1.7.5 —COOR$^{16}$, wherein R$^{16}$ is hydrogen atom or —(C$_1$–C$_{10}$)-alkyl,
   1.7.6 —NO$_2$,
   1.7.7 —S(O)$_y$—R$^{14}$, wherein y is zero, 1 or 2, R$^{14}$ is —(C$_1$–C$_{10}$)-alkyl, phenyl, which phenyl is unsubstituted or mono- to penta-substituted by substituents independently chosen from those defined under 1.7.1 to 1.7.11, amino or —N(R$^{13}$)$_2$,
      wherein R$^{13}$ is independently of one another chosen from hydrogen atom, phenyl, —(C$_1$–C$_{10}$)-alkyl, —C(O)—(C$_1$–C$_7$)-alkyl, —C(O)-phenyl, —C(O)—NH—(C$_1$–C$_7$)-alkyl, —C(O)—O-phenyl, —C(O)—NH-phenyl, —C(O)—O—(C$_1$–C$_7$)-alkyl,
      —S(O)$_y$—R$^{14}$, wherein R$^{14}$ and y are as defined above, and wherein the R$^{13}$ alkyl or phenyl groups in each case are unsubstituted or mono- to penta-substituted by substituents independently chosen from those as defined under 1.7.1 to 1.7.11, or
      R$^{13}$ together with the nitrogen atom to which it is bonded may be independently chosen to form a heterocycle having 5 to 7 ring atoms,
   1.7.8 —O-phenyl, wherein phenyl is unsubstituted or mono- to penta-substituted independently of one another as defined under 1.7.1 to 1.7.11,
   1.7.9 a radical selected from pyrrolidine, tetrahydropyridine, piperidine, piperazine, imidazoline, pyrazolidine, furan, morpholine, pyridine, pyridazine, pyrazine, oxolan, imidazoline, isoxazolidine, 2-isoxazoline, isothiazolidine, 2-isothiazoline, thiophene or thiomorpholine,
   1.7.10 —(C$_3$–C$_7$)-cycloalkyl or
   1.7.11 =O,
1.8. —N(R$^{13}$)$_2$, wherein R$^{13}$ is as defined in 1.7.7 above,
1.9. —NH—C(O)—R$^{15}$, wherein R$^{15}$ is
   1.9.1 a radical selected from pyrrolidine, tetrahydropyridine, piperidine, piperazine, imidazoline, pyrazolidine, furan, morpholine, pyridine, pyridazine, pyrazine, oxolan, imidazoline, isoxazolidine, 2-isoxazoline, isothiazolidine, 2-isothiazoline, thiophene or thiomorpholine,
      wherein said radical is unsubstituted or mono- to penta-substituted by substituents independently chosen from those as defined under 1.7.1 to 1.7.11 above, by —CF$_3$, by benzyl or by —(C$_1$–C$_{10}$)-alkyl, wherein the —(C$_1$–C$_{10}$)-alkyl is mono to tri- substituted by substituents independently chosen from those as defined under 1.7.1 to 1.7.11 above, 1.9.2 —$(C_1–C_{10})$-alkyl, wherein alkyl is unsubstituted or mono- to penta-substituted by substituents independently chosen from those as defined under 1.7.1 to 1.7.11 above or by —O—$(C_1–C_{10})$-alkyl, wherein alkyl is unsubstituted or mono- to penta-substituted by substituents independently chosen from those as defined under 1.7.1 to 1.7.11 above, 1.9.3 —$(C_3–C_7)$-cycloalkyl, 1.9.4 —$N(R^{13})_2$, wherein $R^{13}$ is as defined in 1.7.7 above, or 1.9.5 phenyl, wherein phenyl is unsubstituted or mono- to penta-substituted by substituents independently chosen from those as defined under 1.7.1 to 1.7.11 above, by —O—$(C_1–C_{10})$-alkyl, by —CN, by —$CF_3$, by —$(C_1–C_{10})$-alkyl, wherein alkyl is mono to tri-substituted by substituents independently chosen from those as defined under 1.7.1 to 1.7.11 above, or by two substituents of said phenyl which form a dioxolan ring, 1.10. —$S(O)_y$—$R^{14}$, wherein $R^{14}$ and y are as defined in 1.7.7 above, 1.11. —C(O)—$R^{12}$, wherein $R^{12}$ is phenyl or —$(C_1–C_7)$-alkyl, wherein alkyl or phenyl are unsubstituted or mono- to penta-substituted by substituents independently chosen from those as defined under 1.7.1 to 1.7.11 above, 1.12. —C(O)—O—$R^{12}$, wherein $R^{12}$ is as defined in 1.11. above, 1.13. —$(C_1–C_{10})$-alkyl, wherein alkyl is unsubstituted or mono- to penta-substituted by substituents independently chosen from those as defined under 1.7.1 to 1.7.11 above, 1.14. —O—$(C_1–C_6)$-alkyl-O—$(C_1–C_6)$-alkyl, 1.15. —O—$(C_0–C_4)$-alkyl-$(C_3–C_7)$-cycloalkyl, 1.16. —$(C_1–C_4)$-alkyl-$N(R^{13})_2$, wherein $R^{13}$ is as defined in 1.7.7 above 1.17. —$CF_3$ or 1.18. —$CF_2$—$CF_3$, $R^4$ is 1. —$(C_1–C_{10})$-alkyl, wherein alkyl is mono- to penta-substituted, by substituents independently chosen from those as defined under 1.7.1 to 1.7.11 above, 2. —$CF_3$,
3. —$CF_2$—$CF_3$,
4. —CN,
5. —$S(O)_y$—$R^{14}$, wherein $R^{14}$ and y are as defined in 1.7.7 above,
6. —$NH_2$,
7. —O—$(C_1–C_{10})$-alkyl, wherein alkyl is mono- to penta-substituted by substituents independently chosen from 7.1 phenyl, which is unsubstituted or mono- to penta-substituted by substituents independently chosen from halogen or —O—$(C_1–C_4)$-alkyl, 7.2 halogen,
7.3 —$NH_2$,
7.4 —OH,
7.5 —$COOR^{16}$, wherein $R^{16}$ is hydrogen atom or —$(C_1–C_{10})$-alkyl,
7.6 —$NO_2$,
7.7 —$S(O)_y$—$R^{14}$, wherein y is zero, 1 or 2, $R^{14}$ is —$(C_1–C_{10})$-alkyl, phenyl, which phenyl is unsubstituted or mono- to penta-substituted by substituents independently chosen from those as defined under 1.7.1 to 1.7.11, amino or —$N(R^{13})_2$, wherein $R^{13}$ is independently of one another chosen from hydrogen atom, phenyl, —$(C_1–C_{10})$-alkyl, —C(O)—$(C_1–C_7)$-alkyl, —C(O)-phenyl, —C(O)—NH—$(C_1–C_7)$-alkyl, —C(O)—O-phenyl, —C(O)—NH-phenyl, —C(O)—O—$(C_1–C_7)$-alkyl, —$S(O)_y$—$R^{14}$, wherein $R^{14}$ and y are defined as in 7.7, and wherein the $R^{13}$ alkyl or phenyl groups in each case are unsubstituted or mono- to penta-substituted by substituents independently chosen from those as defined under 1.7.1 to 1.7.11 above, or $R^{13}$ together with the nitrogen atom to which it is bonded form a heterocycle having 5 to 7 ring atoms, 7.8 —O-phenyl, wherein phenyl is unsubstituted or mono- to penta-substituted by substituents independently chosen from those as defined under 1.7.1 to 1.7.11 above, 7.9 a radical selected from pyrrolidine, tetrahydropyridine, piperidine, piperazine, imidazoline, pyrazolidine, furan, morpholine, pyridine, pyridazine, pyrazine, oxolan, imidazoline, isoxazolidine, thiophene, 2-isoxazoline, isothiazolidine, 2-isothiazoline, or thiomorpholine, 7.10 —$(C_3–C_7)$-cycloalkyl or 7.11 =O, 8. —$N(R^{17})_2$, wherein $R^{17}$ is independently of one another chosen from hydrogen atom, phenyl, —$(C_1–C_{10})$-alkyl, —C(O)-phenyl, —C(O)—NH—$(C_1–C_7)$-alkyl, —C(O)—$(C_1–C_{10})$-alkyl, —C(O)—O-phenyl, —C(O)—NH-phenyl, —C(O)—O—$(C_1–C_7)$-alkyl, —$S(O)_y$—$R^{14}$, wherein $R^{14}$ and y are defined as in 7.7 above, and wherein alkyl or phenyl in each case are unsubstituted or mono- to penta-substituted independently of one another as defined under 1.7.1 to 1.7.11 above, or $R^{17}$ together with the nitrogen atom to which it is bonded form a heterocycle having 5 to 7 ring atoms, 9. —NH—C(O)—$R^{15}$, wherein $R^{15}$ is 9.1 a radical selected from pyrrolidine, tetrahydropyridine, piperidine, piperazine, imidazoline, pyrazolidine, furan, morpholine, pyridine, pyridazine, pyrazine, oxolan, imidazoline, isoxazolidine, 2-isoxazoline, isothiazolidine, 2-isothiazoline, thiophene or thiomorpholine, wherein said radical is unsubstituted or mono- to penta-substituted by substituents independently chosen from those as defined under 1.7.1 to 1.7.11 above, —$CF_3$, benzyl or by —$(C_1–C_{10})$-alkyl, wherein alkyl is mono to tri-substituted by substituents independently chosen from those as, defined under 1.7.1 to 1.7.11 above, 9.2 —$(C_1–C_{10})$-alkyl, wherein alkyl is mono- to penta-substituted by substituents independently chosen from those as defined under 1.7.1 to 1.7.11 above or by —O—$(C_1–C_{10})$-alkyl, wherein alkyl is unsubstituted or mono- to penta-substituted by substituents independently chosen from those as defined under 1.7.1 to 1.7.11 above, 9.3 —$(C_3–C_7)$-cycloalkyl, 9.4 —$N(R^{13})_2$, wherein $R^{13}$ is as defined in 1.7.7 above provided that —$N(R^{13})_2$ is not —$NH_2$, or 9.5 phenyl, wherein phenyl is unsubstituted or mono- to penta-substituted by substituents independently chosen from those as defined under 1.7.1 to 1.7.11 above, by —O—$(C_1–C_{10})$-alkyl, by —CN, by —CF$_3$, by —(C$_1$–C$_{10}$)-alkyl, wherein alkyl is mono to tri-substituted by substituents independently chosen from those as defined under 1.7.1 to 1.7.11 above, or by two substituents of the phenyl radical which form a dioxolan ring 10. —C(O)—R$^{12}$, wherein R$^{12}$ is phenyl or —(C$_1$–C$_7$)-alkyl, wherein phenyl or alkyl are mono- to penta-substituted by substituents independently chosen from those as defined under 1.7.1 to 1.7.11 above,
11. —C(O)—O—R$^{12}$, wherein R$^{12}$ is as defined in 10, above,
12. —O—(C$_1$–C$_6$)-alkyl-O—(C$_1$–C$_6$)-alkyl,
13. —O—(C$_0$–C$_4$)-alkyl-(C$_3$–C$_7$)-cycloalkyl or
14. —(C$_1$–C$_4$)-alkyl-N(R$^{13}$)$_2$, wherein R$^{13}$ is as defined in 1.7.7 above, R$^5$ is 1. a hydrogen atom,
2. —(C$_1$–C$_{10}$)-alkyl, wherein alkyl is unsubstituted or mono- to penta-substituted by substituents independently chosen from those as defined under 1.7.1 to 1.7.4 above,
3. —C(O)—R$^9$, wherein R$^9$ is —NH$_2$, —(C$_1$–C$_{10}$)-alkyl, wherein alkyl is unsubstituted or mono- to penta-substituted by substituents independently chosen from those as defined under 7.1 to 7.4, or —N(R$^{13}$)$_2$, wherein R$^{13}$ is as defined in 1.7.7 above, or
4. —S(O)$_2$—R$^9$, wherein R$^9$ is as defined in 3. above, or R$^4$ and R$^5$ together with the atom to which they are bonded form a heterocycle, or R$^3$ and R$^5$ together with the atom to which they are bonded form a heterocycle containing an additional oxygen atom in the ring and R$^6$, R$^7$ and R$^8$ independently of one another are chosen from hydrogen atom or methyl, or in case b)
the substituents R$^1$, R$^2$ and R$^4$ may be independently chosen as defined under 1.1 to 1.18 in case a) above, R$^3$ is 1. —CF$_3$,
2. —CF$_2$—CF$_3$,
3. —CN,
4. —COOH,
5. —NO$_2$,
6. —NH$_2$,
7. —O—(C$_1$–C$_{10}$)-alkyl, wherein alkyl is mono- to penta substituted by substituents independently chosen from
    7.1 phenyl, which is unsubstituted or mono- to penta-substituted by substituents independently chosen from halogen or —O—(C$_1$–C$_4$)-alkyl,
    7.2 halogen,
    7.3 —NH$_2$,
    7.4 —OH,
    7.5 —COOR$^{16}$, wherein R$^{16}$ is hydogen atom or —(C$_1$–C$_{10}$)-alkyl,
    7.6 —NO$_2$,
    7.7 —S(O)$_y$—R$^{14}$, wherein y is zero, 1 or 2, R$^{14}$ is —(C$_1$–C$_{10}$)-alkyl, phenyl, which phenyl is unsubstituted or mono- to penta-substituted by substituents independently chosen from those as defined under 1.7.1 to 1.7.11, amino or —N(R$^{13}$)$_2$, wherein R$^{13}$ is independently of one another chosen from hydrogen atom, phenyl, —(C$_1$–C$_{10}$)-alkyl, —C(O)—(C$_1$–C$_7$)-alkyl, —C(O)-phenyl, —C(O)—NH—(C$_1$–C$_7$)-alkyl, —C(O)—O-phenyl, —C(O)—NH-phenyl, —C(O)—O—(C$_1$–C$_7$)-alkyl, —S(O)$_y$—R$^{14}$, wherein R$^{14}$ and y are defined as in 7.7,
    and wherein the R$^{13}$ alkyl or phenyl groups in each case are unsubstituted or mono- to penta-substituted by substituents independently chosen from those as defined under 1.7.1 to 1.7.11 above, or R$^{13}$ together with the nitrogen atom to which it is bonded form a heterocycle having 5 to 7 ring atoms,
    7.8 —O-phenyl, wherein phenyl is unsubstituted or mono- to penta-substituted by substituents independently chosen from those as defined under 1.7.1 to 1.7.11 above,
    7.9 a radical selected from pyrrolidine, tetrahydropyridine, piperidine, piperazine, imidazoline, pyrazolidine, furan, morpholine, pyridine, pyridazine, pyrazine, oxolan, imidazoline, isoxazolidine, 2-isoxazoline, isothiazolidine, 2-isothiazoline, thiophene or thiomorpholine,
    7.10 —(C$_3$–C$_7$)-cycloalkyl or
    7.11 =O,
8. —N(R$^{13}$)$_2$, wherein R$^{13}$ is as defined in 1.7.7 above,
9. —NH—C(O)—R$^{15}$, wherein R$^{15}$ is
    9.1 a radical selected from pyrrolidine, tetrahydropyridine, piperidine, piperazine, imidazoline, pyrazolidine, furan, morpholine, pyridine, pyridazine, pyrazine, oxolan, imidazoline, isoxazolidine, 2-isoxazoline, isothiazolidine, 2-isothiazoline, thiophene or thiomorpholine, wherein said radical is unsubstituted or mono- to penta-substituted by substituents independently chosen from those as defined under 1.7.1 to 1.7.11 above, —CF$_3$, benzyl or by —(C$_1$–C$_{10}$)-alkyl, wherein alkyl is mono to tri-substituted by substituents independently chosen from those as defined under 1.7.1 to 1.7.11 above,
    9.2 —(C$_1$–C$_{10}$)-alkyl, wherein alkyl is unsubstituted or mono- to penta-substituted by substituents independently chosen from those as defined under 1.7.1 to 1.7.11 above or by —O—(C$_1$–C$_{10}$)-alkyl, wherein alkyl is unsubstituted or mono- to penta-substituted by substituents independently chosen from those as defined under 1.7.1 to 1.7.11 above,
    9.3 —(C$_3$–C$_7$)-cycloalkyl,
    9.4 —N(R$^{13}$)$_2$, wherein R$^{13}$ is as defined in 1.7.7 above, or
    9.5 phenyl, wherein phenyl is unsubstituted or mono- to penta-substituted by substituents independently chosen from those as defined under 1.7.1 to 1.7.11 above, by —O—(C$_1$–C$_{10}$)-alkyl, by —CN, by —CF$_3$, by —(C$_1$–C$_{10}$)-alkyl, wherein alkyl is mono to tri-substituted by substituents independently chosen from those as defined under 1.7.1 to 1.7.11 above, or by two substituents of the phenyl radical which form a dioxolan ring
10. —S(O)y-R$^{14}$, wherein R$^{14}$ and y are as defined in 1.7.7 above,
11. —C(O)—R$^{12}$, wherein R$^{12}$ is phenyl or —(C$_1$–C$_7$)-alkyl, wherein phenyl or alkyl are unsubstituted or mono- to penta-substituted by substituents independently chosen from those as defined under 1.7.1 to 1.7.11 above,
12. —C(O)—O—R$^{12}$, wherein R$^{12}$ is as defined in 11. above,
13. —(C$_1$–C$_{10}$)-alkyl, wherein alkyl is unsubstituted or mono- to penta-substituted by substituents independently chosen from those as defined under 1.7.1 to 1.7.11 above,
14. —O—(C$_1$–C$_6$)-alkyl-O—(C$_1$–C$_6$)-alkyl, 15. —O—($C_0$–$C_4$)-alkyl-($C_3$–$C_7$)-cycloalkyl or
16. —($C_1$–$C_4$)-alkyl-N($R^{13}$)$_2$, wherein $R^{13}$ is as defined in 1.7.7 above, $R^5$ is defined as $R^5$ in case a) above, $R^6$, $R^7$ and $R^8$ independently of one another are chosen from hydrogen atom or methyl.

Examples Include Compounds of Formula I, wherein in Case a)

$B_6$, $B_7$, $B_8$, and $B_9$ are each a carbon atom, $R^1$, $R^2$ and $R^3$ independently of one another are chosen from hydrogen atom, halogen, cyano, nitro, amino, —O—($C_1$–$C_7$)-alkyl, wherein alkyl is unsubstituted or substituted by phenyl, —$CF_2$—$CF_3$, —$CF_3$, —N($R^{18}$)$_2$,
  wherein $R^{18}$ is independently of one another chosen from hydrogen atom, —($C_1$–$C_7$)-alkyl, phenyl, —C(O)-phenyl, —C(O)-pyridyl, —C(O)—NH-phenyl, —C(O)—O-phenyl, —C(O)—O—($C_1$–$C_4$)-alkyl or —C(O)—($C_1$–$C_7$)-alkyl, wherein alkyl, pyridyl or phenyl are unsubstituted or mono- to tri-substituted by substituents independently chosen from those as defined under 1.7.1 to 1.7.11, or $R^{18}$ together with the nitrogen atom to which it is bonded form a heterocycle having 5 to 7 ring atoms,
  S(O)$_y$—$R^{14}$,
    wherein y is zero, 1 or 2, and $R^{14}$ is —($C_1$–$C_{10}$)-alkyl, phenyl, which phenyl is.unsubstituted or mono- to penta-substituted by substituents independently chosen from those as defined under 1.7.1 to 1.7.1.1, amino or —N($R^{18}$)$_2$,
    wherein $R^{18}$ is as defined above,
    wherein alkyl is unsubstituted or mono- to tri-substituted independently of one another as defined under 1.7.1 to 1.7.11, or —C(O)—O—$R^{12}$, wherein $R^{12}$ is as defined as in 1.11 above, $R^4$ is cyano, amino, —O—($C_1$–$C_7$)-alkyl, wherein alkyl is substituted by phenyl, —$CF_2$—$CF_3$, —$CF_3$, —N($R^{18}$)$_2$,
  wherein $R^{18}$ is independently of one another chosen from hydrogen atom, —($C_1$–$C_7$)-alkyl, phenyl, —C(O)-phenyl, —C(O)-pyridyl, —C(O)—NH-phenyl, —C(O)—O-phenyl, —C(O)—O—($C_1$–$C_4$)-alkyl or —C(O)—($C_1$–$C_7$)-alkyl, wherein each alkyl, pyridyl or phenyl are unsubstituted or mono- to tri-substituted independently of one another as defined under 1.7.1 to 1.7.11, or $R^{18}$ together with the nitrogen atom to which it is bonded form a heterocycle having 5 to 7 ring atoms,
  S(O)$_y$—$R^{14}$,
    wherein y is zero, 1 or 2, and $R^{14}$ is —($C_1$–$C_{10}$)-alkyl, phenyl, which phenyl is unsubstituted or mono- to penta-substituted by substituents independently chosen from those as defined under 1.7.1 to 1.7.11, amino or —N($R^{18}$)$_2$,
    wherein $R^{18}$ is as defined above,
    wherein alkyl is unsubstituted or mono- to tri-substituted by substituents independently chosen from those as defined under 1.7.1 to 1.7.11, or
  —C(O)—O—$R^{12}$, wherein $R^{12}$ is as defined above, $R^6$, $R^7$ and $R^8$ independently of one another are chosen from hydrogen atom or methyl, and $R^5$ is as defined as for case a) above, or in case b)

the substituents $R^1$, $R^2$ and $R^4$ independently of one another are hydrogen atom, halogen, cyano, nitro, amino, —O—($C_1$–$C_7$)-alkyl, wherein alkyl is unsubstituted or substituted by phenyl, —$CF_2$—$CF_3$, —$CF_3$, —N($R^{18}$)$_2$,
  wherein $R^{18}$ is independently of one another chosen from hydrogen atom, —($C_1$–$C_7$)-alkyl, phenyl, —C(O)-phenyl, —C(O)-pyridyl, —C(O)—NH-phenyl, —C(O)—O-phenyl, —C(O)—O—($C_1$–$C_4$)-alkyl or —C(O)—($C_1$–$C_7$)-alkyl, wherein each alkyl, pyridyl or phenyl are unsubstituted or mono- to tri-substituted independently of one another as defined under 1.7.1 to 1.7.1 1, or $R^{18}$ together with the nitrogen atom to which it is bonded form a heterocycle having 5 to 7 ring atoms,
  S(O)$_y$—$R^{14}$,
    wherein y is zero, 1 or 2, and $R^{14}$ is —($C_1$–$C_{10}$)-alkyl, phenyl, which phenyl is unsubstituted or mono- to penta-substituted by substituents independently chosen from those as defined under 1.7.1 to 1.7.11, amino or —N($R^{18}$)$_2$,
    wherein $R^{18}$ is as defined above,
    wherein alkyl is unsubstituted or mono- to tri-substituted by substituents independently chosen from those as defined under 1.7.1 to 1.7.11, or
  —C(O)—O—$R^{12}$, wherein $R^{12}$ is as defined above, $R^3$ is cyano, nitro, amino, —O—($C_1$–$C_7$)-alkyl, wherein alkyl is substituted by phenyl, —$CF_2$—$CF_3$, —$CF_3$, —N($R^{18}$)$_2$,
  wherein $R^{18}$ is independently of one another chosen from hydrogen, atom,
  —($C_1$–$C_7$)-alkyl, phenyl, —C(O)-phenyl,—C(O)-pyridyl, —C(O)—NH-phenyl, —C(O)—O-phenyl, —C(O)—O—($C_1$–$C_4$)-alkyl or —C(O)—($C_1$–$C_7$)-alkyl, wherein each alkyl, pyridyl or phenyl are unsubstituted or mono- to tri-substituted by substituents independently chosen from those as defined under 1.7.1 to 1.7.11, or $R^{18}$ together with the nitrogen atom to which it is bonded form a heterocycle having 5 to 7 ring atoms,
  S(O)$_y$—$R^{14}$,
    wherein y is zero, 1 or 2, and $R^{14}$ is —($C_1$–$C_{10}$)-alkyl, phenyl, which phenyl is unsubstituted or mono- to penta-substituted by substituents independently chosen from those as defined under 1.7.1 to 1.7.11, amino or —N($R^{18}$)$_2$,
    wherein $R^{18}$ is as defined above,
    wherein alkyl is unsubstituted or mono- to tri-substituted independently of one another as defined under 1.7.1 to 1.7.11, or
  —C(O)—O—$R^{12}$, wherein $R^{12}$ is as defined above, $R^6$, $R^7$ and $R^8$ independently of one another are chosen from hydrogen atom or methyl, and $R^5$ is as defined above.

Further examples include compounds of formula (II)

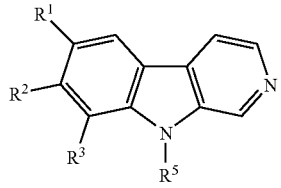

(II)

and/or a stereoisomeric form of the compound of the formula II and/or a physiologically tolerable salt of the compound of the formula II, wherein;

$R^1$ and $R^2$ are independently of one another chosen from hydrogen atom, halogen, cyano, amino, —O—($C_1$–$C_4$)-alkyl, nitro, —$CF_3$, —$CF_2$—$CF_3$, —S(O)$_y$—$R^{14}$, wherein y is 1 or 2, $R^{14}$ is amino, —($C_1$-$C_7$)-alkyl or phenyl, which phenyl is unsubstituted or mono- to tri-substituted as defined for substituents under 1.7.1 to 1.7.11 above,
—N($R^{18}$)$_2$, wherein $R^{18}$ is independently of one another chosen from hydrogen atom, —($C_1$-$C_7$)-alkyl-C(O)—($C_1$-$C_7$)-alkyl, —C(O)-phenyl, C(O)-pyridyl, —C(O)—NH—($C_1$-$C_4$)-alkyl, —C(O)—O-phenyl, —C(O)—O—($C_1$-$C_4$)-alkyl or —($C_1$-$C_{10}$)-alkyl, wherein pyridyl, alkyl or phenyl are unsubstituted or mono- to tri-substituted independently of one another as defined under 1.7.1 to 1.7.11, or $R^{18}$ together with nitrogen atom to which it is bonded form a heterocycle having 5 to 7 ring atoms, $R^3$ is cyano, amino, —O—($C_1$-$C_4$)-alkyl, nitro, —$CF_3$, —$CF_2$—$CF_3$, —S(O)$_y$—$R^{14}$, wherein y is 1 or 2, $R^{14}$ is amino, —($C_1$-$C_7$)-alkyl or phenyl, which phenyl is unsubstituted or mono- to tri-substituted as defined for substituents under 1.7.1 to 1.7.11 above,
—N($R^{18}$)$_2$, wherein $R^{18}$ is independently of one another chosen from hydrogen atom,
—($C_1$-$C_7$)-alkyl-C(O)—($C_1$-$C_7$)-alkyl, —C(O)-phenyl, —C(O)-pyridyl,
—C(O)—O-phenyl, —C(O)—NH—($C_1$-$C_4$)-alkyl, —C(O)—O—($C_1$-$C_4$)-alkyl or
—($C_1$-$C_{10}$)-alkyl, wherein pyridyl, alkyl or phenyl are unsubstituted or mono- to tri-substituted by substituents independently chosen from those as defined under 1.7.1 to 1.7.11, or
$R^{18}$ together with nitrogen atom to which it is bonded form a heterocycle having 5 to 7 ring atoms, and $R^5$ is hydrogen atom, —($C_1$-$C_{10}$)-alkyl,
wherein alkyl is unsubstituted or mono- to tri-substituted by substituents independently chosen from those as defined under 1.7.1 to 1.7.4,
—C(O)—$R^9$ or —S(O)$_2$—$R^9$, wherein $R^9$ is —($C_1$-$C_{10}$)-alkyl, —O—($C_1$-$C_{10}$)-alkyl, wherein alkyl is unsubstituted or mono- to tri-substituted independently of one another as defined under 1.7.1 to 1.7.4, or phenyl, which is unsubstituted or mono- to tri-substituted as defined under 1.7.1 to 1.7.11, or —N($R^{18}$)$_2$, wherein $R^{18}$ is as defined above.

Still further examples are compounds of formula (II), wherein
$R^1$ is bromo, —$CF_3$ or chloro,
$R^2$ is hydrogen atom or O—($C_1$-$C_2$)-alkyl,
$R^3$ is —N($R^{18}$)$_2$, wherein $R^{18}$ is independently of one another chosen from hydrogen atom, —N—C(O)-pyridyl, —C(O)-phenyl, —($C_1$-$C_7$)-alkyl, —C(O)—($C_1$-$C_4$)-alkyl or —C(O)—O—($C_1$-$C_4$)-alkyl, wherein alkyl or phenyl are unsubstituted or mono- to tri-substituted by substituents independently chosen from halogen or —O—($C_1$-$C_2$)-alkyl, and
$R^5$ is hydrogen atom, methyl or —S(O)$_2$—$CH_3$.

Specific compounds and all pharmaceutically acceptable salts thereof which are illustrative of the compounds of the invention include the following;

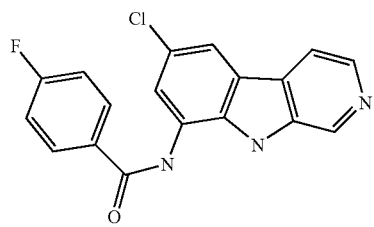

-continued

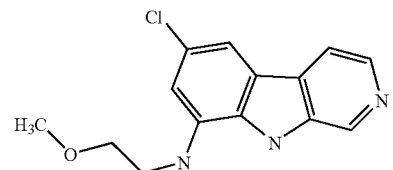

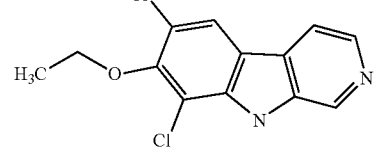

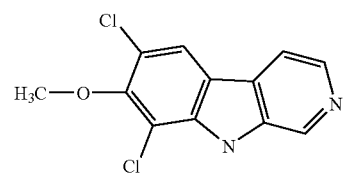

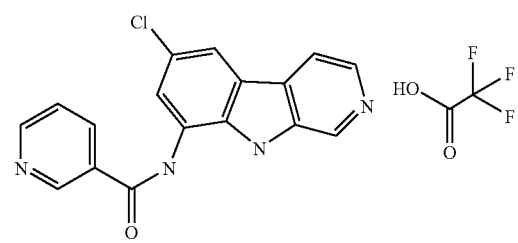

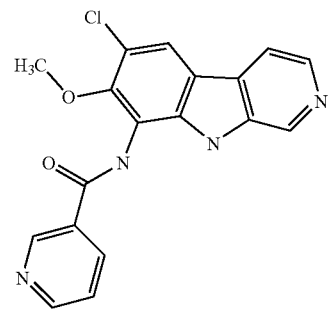

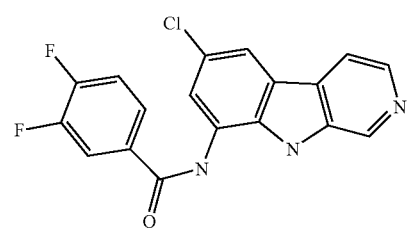

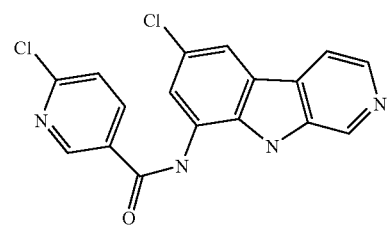

Further specific examples include the following compounds:

N-(6-Chloro-9H-β-carbolin-8-yl)-nicotinamide, as well as the bismesylate salt, bistrifluoracetate salt and bishydrochloride salt of N-(6-Chloro-9H-β-carbolin-8-yl)-nicotinamide, N-(6-Chloro-9H-β-carbolin-8-yl)-3,4-difluoro-benzamide, as well as the hydrochloride salt of N-(6-Chloro-9H-β-carbolin-8-yl)-3,4-difluoro-benzamide, N-(6-Chloro-7-methoxy-9H-β-carbolin-8-yl)-nicotinamide as well as the bistrifluoracetate salt and bishydrochloride salt of N-(6-Chloro-7-methoxy-9H-β-carbolin-8-yl)-nicotinamide and 6-Chloro-N-(6-chloro-9H-β-carbolin-8-yl)-nicotinamide.

The term "alkyl" by itself or as part on another substituent, unless otherwise stated means a straight or branched chain hydrocarbon radical having 1 to 10 carbon atoms such as methyl, ethyl, n-propyl, isopropyl, n-butyl, tertiary-butyl, pentyl, hexyl, heptyl, nonyl, octyl, decanyl or cycloalkyl having 3 to 7 carbon atoms such as cylopropyl, cyclobutyl, cyclohexyl or cycloheptyl.

The term "alkoxy" by itself or as part on another substituent, unless otherwise stated means —O-alkyl or —O-substituted alkyl.

The term "heterocycle having 5 to 7 ring atoms" represents a radical of a monocyclic saturated system having 5 to 7 ring members, which contains 1, 2 or 3 heteroatoms as ring members. Examples of heteroatoms are N, O and S. Examples of the term heterocycle having 5 to 7 ring atoms are pyrrolidine, tetrahydropyridine, piperidine, piperazine, imidazoline, pyrazolidine, furan, morpholine, pyridine, pyridazine, pyrazine, oxolan, imidazoline, isoxazolidine, 2-isoxazoline, isothiazolidine, 2-isothiazoline, thiophene or thiomorpholine.

The term "aryl" by itself or as part on another substituent, unless otherwise stated refers to an organic radical derived from an aromatic molecule by removal of one atom; such as phenyl, pyridyl, thiazoly, morpholinyl and naphthyl.

The term "substituted alkyl" means an alkyl radical substituted at one or more positions by one or more radicals of the group halogen, nitro, sulfo, amino, substituted amino, carboxyl, alkoxy, —O-aryl, —O-substituted aryl, and hydroxyl.

The term "substituted aryl" means an aryl radical substituted at one or more positions by one or more radicals of the group halogen, alkyl, substituted alkyl, nitro, sulfo, amino, alkoxy, aryl, substituted aryl, or hydroxyl groups, such as an aryl radical substituted at 1 to 3 positions by 1 to 3 groups.

The term "substituted amino" refers to —N($R^{13}$)$_2$ wherein $R^{13}$ is independently of one another chosen from hydrogen atom, sulfo, alkyl, aryl, —C(O)-alkyl, C(O)—NH-aryl, —C(O)—O-aryl, —C(O)—O-alkyl, or C(O)—O-aryl, wherein each alkyl or aryl may be independently substituted.

The term "sulfo" refers to —S(O)y-$R^{14}$, wherein $R^{14}$ is an alkyl, aryl, substituted aryl, substituted alkyl, amino, or substituted amino and y is zero, one or two.

The term "halogen" is understood as meaning fluorine, chlorine, bromine or iodine.

The term "—($C_1$–$C_4$)-alkyl" is understood as meaning hydrocarbon radicals whose carbon chain is linear or branched and contains 1 to 4 carbon atoms.

The invention further relates to a process for the preparation of the compounds of formula I and/or stereoisomeric forms of the compounds of the formula I and/or physiologically tolerable salts of the compounds of formula I, which comprises a) reacting a compound of formula III

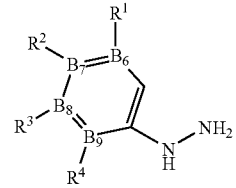

(III)

in which $R^1$, $R^2$, $R^3$, $R^4$, $B_6$, $B_7$, $B_8$ and $B_9$ are each as defined in formula I, with a compound of the formula IV,

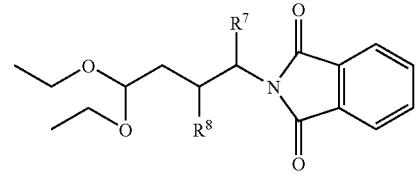

(IV)

in the presence of a acid, to yield a compound of the formula V

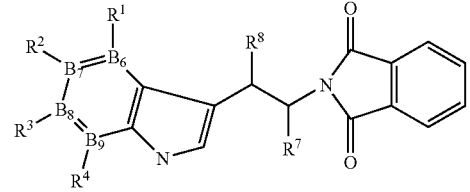

(V)

which is reacted with hydrazine hydrate and later with formaldehyde ($R^6$ is H) or $R^6$CHO to give a compound of formula VI

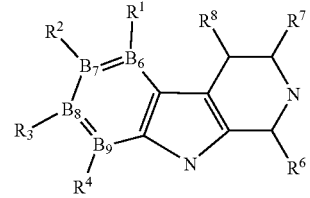

(VI)

and oxidized to give a compound of the formula VII,

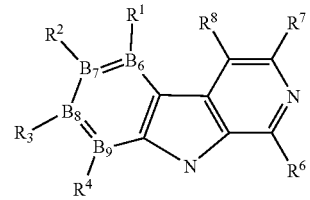

(VII)

where $R^1$ to $R^4$, R6 to R8 and $B_6$ to $B_9$ are as defined in formula I, a compound of formula (I), or b) a compound of the formula VII is reacted with a compound of the formula VIII

Y—$R^5$ (VIII)

where Y is halogen or —OH and $R^5$ is as defined in formula I, to give a compound of the formula I, or c) resolving a compound of the formula I, which on account of its chemical structure occurs in enantiomeric forms, prepared by process a) or b) into the pure enantiomers by salt formation with enantiomerically pure acids or bases, chromatography on chiral stationary phases or derivatization by means of chiral enantiomerically pure compounds such as amino acids, separation of the diastereomers thus obtained, and removal of the chiral auxiliary groups, or d) isolating the compound of the formula I prepared by process a), b) or c) either in free form or, in the case of the presence of acidic or basic groups, converting it into physiologically tolerable salts.

The preparation of physiologically tolerable salts of compounds of the formula I capable of salt formation, including their stereoisomeric forms, is carried out in a manner known per se. With basic reagents such as hydroxides, carbonates, hydrogencarbonates, alkoxides and also ammonia or organic bases, for example trimethyl- or triethylamine, ethanolamine or triethanolamine or alternatively basic amino acids, for example lysine, ornithine or arginine, the carboxylic acids form stable alkali metal, alkaline earth metal or optionally substituted ammonium salts. If the compounds of the formula I contain basic groups, stable acid addition salts can also be prepared using strong acids. For this, both inorganic and organic acids such as hydrochloric, hydrobromic, sulfuric, phosphoric, methanesulfonic, benzenesulfonic, p-toluenesulfonic, 4-bromobenzenesulfonic, cyclohexylamidosulfonic, trifluoromethylsulfonic, acetic, oxalic, tartaric, succinic or trifluoroacetic acid are suitable.

The invention also relates to pharmaceuticals which comprise an efficacious amount of at least one compound of the formula I and/or of a physiologically tolerable salt of the compounds of the formula I and/or an optionally stereoisomeric form of the compounds of the formula I, together with a pharmaceutically suitable and physiologically tolerable excipient, additive and/or other active compounds and auxiliaries.

On account of the pharmacological properties, the compounds according to the invention are suitable for the prophylaxis and therapy of all those disorders in whose course an increased activity of IkB kinase is involved. These include, for example, asthma, rheumatoid arthritis (in the case of inflammation), osteoarthritis, Alzheimer's disease, carcinomatous disorders (potentiation of cytotoxic therapies), cardiac infarct or atherosclerosis.

The pharmaceuticals according to the invention are in general administered orally or parentally or by rectal, inhale or transdermal administration.

The invention also relates to the use of the compounds of the formula I

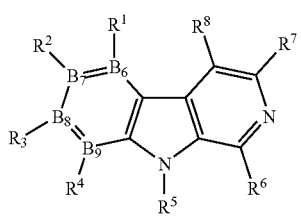

and/or a stereoisomeric form of the compounds of the formula I and/or a physiologically tolerable salt of the compounds of the formula I, for the production of pharmaceuticals for the prophylaxis and therapy of disorders in whose course an increased activity of $I_kB$ kinase is involved, wherein $B_6$, $B_7$, $B_8$ and $B_9$ are independently selected from the group consisting of carbon atom and nitrogen atom and wherein $B_6$, $B_7$, $B_8$ and $B_9$ together are no more than two nitrogen atoms at the same time;

where the substituents $R^1$, $R^2$, $R^3$, $R^4$ and $R^8$ may be independently chosen from
1. hydrogen atom,
2. halogen,
3. —OH,
4. —CN,
5. sulfo,
6. —$NO_2$,
7. —$NH_2$,
8. alkoxy,
9. substituted amino,
10. —NH—C(O)—$R^{15}$, wherein $R^{15}$ is a heterocycle having 5 to 7 ring atoms, an alkyl, an aryl, a substituted aryl or a substituted alkyl,
11. —COOH,
12. —O—$R^{10}$, wherein $R^{10}$ is alkyl, substituted alkyl or aryl,
13. —C(O)—$R^{12}$, wherein $R^{12}$ is alkyl, substituted alkyl or aryl,
14. —C(O)—O—$R^{12}$, wherein $R^{12}$ is as defined in 13, above,
15. aryl,
16. —O-aryl,
17. substituted aryl,
18. —O-substituted aryl,
19. alkyl,
20. substituted alkyl,
21. —$CF_3$ or
22. —$CF_2$—$CF_3$, provided that at least one of $R^1$, $R^2$, $R^3$, $R^4$ and $R^8$ is not a hydrogen atom, $R^5$ is
1. hydrogen atom,
2. alkyl,
3. alkyl radical, substituted at one or more positions by one or more of the radicals, halogen, amino or hydroxyl,
4. —C(O)—$R^9$ or
5. —$S(O)_2$—$R^9$, in which
    $R^9$ is
    a) alkyl,
    b) alkyl radical, substituted at one or more positions by one or more of the radicals, halogen, amino or hydroxyl,
    c) aryl,
    d) aryl radical, substituted at one or more positions by one or more of the radicals, halogen, amino, or hydroxyl,
    e) —$NH_2$,
    f) alkoxy or
    g) substituted amino, and $R^6$ and $R^7$ may be independently chosen from
1. hydrogen atom,
2. halogen,
3. —OH,
4. methyl,
5. —O—$(C_1$–$C_{10})$-alkyl, wherein alkyl is unsubstituted or mono- to tri-substituted by substituents independently chosen from 5.1 aryl,
5.2 halogen,
5.3 —$NO_2$,
5.4 sulfo,
5.5 —COOH,
5.6 —$NH_2$,
5.7 —O—($C_1$–$C_4$)-alkyl or
5.8 —OH, or
6. —$N(R^{13})_2$, wherein $R^{13}$ is independently of one another chosen from hydrogen atom, aryl, —C(O)—($C_1$–$C_4$)-alkyl or substituted aryl or alkyl, wherein said —C(O)—($C_1$–$C_4$)-alkyl is unsubstituted or mono- to tri-substituted independently of one another as defined under 5.1 to 5.8, or
$R^{13}$ together with the nitrogen atom to which it is bonded form a heterocycle having 5 to 7 ring atoms.

Following are examples of the use of the compounds of formula I, wherein
$B_6$, $B_7$, $B_8$, and $B_9$ are each a carbon atom,
$R^1$, $R^2$, $R^3$, $R^4$ and $R^8$ are independently chosen from
1. hydrogen atom,
2. halogen,
3. —CN,
4. —COOH,
5. —$NO_2$,
6. —$NH_2$,
7. —O—($C_1$–$C_{10}$)-alkyl, wherein alkyl is unsubstituted or mono- to penta-substituted by substituents independently chosen from
   7.1 phenyl, which is unsubstituted or mono- to penta-substituted by substituents independently chosen from halogen or —O—($C_1$–$C_4$)-alkyl,
   7.2 halogen,
   7.3 —$NH_2$,
   7.4 —OH,
   7.5 —$COOR^{16}$, wherein $R^{16}$ is hydogen atom or —($C_1$–$C_{10}$)-alkyl,
   7.6 —$NO_2$,
   7.7 —$S(O)_y$—$R^{14}$, wherein y is zero, 1 or 2, $R^{14}$ is —($C_1$–$C_{10}$)-alkyl, phenyl, which phenyl is unsubstituted or mono- to penta-substituted by substituents independently chosen from those as defined under 7.1 to 7.11, amino or —$N(R^{13})_2$,
   wherein $R^{13}$ is independently of one another chosen from hydrogen atom, phenyl, —($C_1$–$C_{10}$)-alkyl, —C(O)—($C_1$–$C_7$)-alkyl, —C(O)-phenyl, —C(O)—NH—($C_1$–$C_7$)-alkyl, —C(O)—O-phenyl, —C(O)—NH-phenyl, —C(O)—O—($C_1$–$C_7$)-alkyl, —$S(O)_y$—$R^{14}$, wherein $R^{14}$ and y are as defined above,
   and wherein R13 alkyl or phenyl groups in each case are unsubstituted or mono- to penta-substituted by substituents independently chosen from those as defined under 7.1 to 7.11 above, or
   $R^{13}$ together with the nitrogen atom to which it is bonded form a heterocycle having 5 to 7 ring atoms,
   7.8 —O-phenyl, wherein phenyl is unsubstituted or mono- to penta-substituted by substituents independently chosen from those as defined under 7.1 to 7.11 above,
   7.9 a radical selected from pyrrolidine, tetrahydropyridine, piperidine, piperazine, imidazoline, pyrazolidine, furan, morpholine, pyridine, pyridazine, pyrazine, oxolan, imidazoline, isoxazolidine, 2-isoxazoline, isothiazolidine, 2-isothiazoline, thiophene or thiomorpholine,
   7.10 —($C_3$–$C_7$)-cycloalkyl or
   7.11 =O,
8. —$N(R^{13})_2$, wherein $R^{13}$ is as defined in 7.7 above,
9. —NH—C(O)—$R^{15}$, wherein $R^{15}$ is
   9.1 a radical selected from pyrrolidine, tetrahydropyridine, piperidine, piperazine, imidazoline, pyrazolidine, furan, morpholine, pyridine, pyridazine, pyrazine, oxolan, imidazoline, isoxazolidine, 2-isoxazoline, isothiazolidine, 2-isothiazoline, thiophene or thiomorpholine, wherein said radical is unsubstituted or mono- to penta-substituted by substituents independently chosen from those as defined under 7.1 to 7.11 above, —$CF_3$, benzyl or by —($C_1$–$C_{10}$)-alkyl, wherein alkyl is mono to tri-substituted independently of one another as defined under 7.1 to 7.11 above,
   9.2 —($C_1$–$C_{10}$)-alkyl, wherein alkyl is unsubstituted or mono- to penta-substituted by substituents independently chosen from those as defined under 7.1 to 7.11 above or by —O—($C_1$–$C_{10}$)-alkyl, wherein alkyl is unsubstituted or mono- to penta-substituted by substituents independently chosen from those as defined under 7.1 to 7.11 above,
   9.3 —($C_3$–$C_7$)-cycloalkyl,
   9.4 —$N(R^{13})_2$, wherein $R^{13}$ is as defined in 7.7 above, or
   9.5 phenyl, wherein phenyl is unsubstituted or mono- to penta-substituted by substituents independently chosen from those as defined under 7.1 to 7.11 above, by —O—($C_1$–$C_{10}$)-alkyl, by —CN, by —$CF_3$, by —($C_1$–$C_{10}$)-alkyl, wherein alkyl is mono to tri-substituted by substituents independently chosen from those as defined under 7.1 to 7.11 above, or by two substituents of the phenyl radical which form a dioxolan ring,
10. —$S(O)y$-$R^{14}$, wherein $R^{14}$ and y are as defined in 7.7 above,
11. —C(O)—$R^{12}$, wherein $R^{12}$ is phenyl or —($C_1$–$C_7$)-alkyl, wherein phenyl or alkyl are unsubstituted or mono- to penta-substituted by substituents independently chosen from those as defined under 7.1 to 7.11 above,
12. —C(O)—O—$R^{12}$, wherein $R^{12}$ is as defined in 11, above,
13. —($C_1$–$C_{10}$)-alkyl, wherein alkyl is unsubstituted or mono- to penta-substituted by substituents independently chosen from those as defined under 7.1 to 7.11 above,
14. —O—($C_1$–$C_6$)-alkyl-O—($C_1$–$C_6$)-alkyl,
15. —O—($C_0$–$C_4$)-alkyl-($C_3$–$C_7$)-cycloalkyl,
16. —($C_1$–$C_4$)-alkyl-$N(R^{13})_2$, wherein $R^{13}$ is as defined in 7.7 above
17. —$CF_3$ or
18. —$CF_2$—$CF_3$,
provided that at least one of $R^1$, $R^2$, $R^3$, $R^4$ and $R^8$ is not a hydrogen atom,
$R^5$ is
1. hydrogen atom,
2. —($C_1$–$C_{10}$)-alkyl, wherein alkyl is unsubstituted or mono- to penta-substituted by substituents independently chosen from those as defined under 7.1 to 7.4 above,
3. —C(O)—$R^9$, wherein $R^9$ is —$NH_2$, —($C_1$–$C_{10}$)-alkyl, wherein alkyl is unsubstituted or mono- to penta-substituted by substituents independently chosen from those as defined under 7.1 to 7.4, or —$N(R^{13})_2$, wherein $R^{13}$ is as defined in 7.7 above, or
4. —$S(O)_2$—$R^9$, wherein $R^9$ is as defined in 3 above, or $R^4$ and $R^5$ together with the atom to which they are bonded form a heterocycle, or $R^3$ and $R^5$ together with the atom to which they are bonded form a heterocycle containing an additional oxygen atom in the ring and $R^6$ and $R^7$ independently of one another are chosen from hydrogen atom or methyl.

Further examples include the use of compounds of formula I for the production of pharmaceuticals for the prophylaxis and therapy of disorders in whose course an increased activity of $I_kB$ kinase is involved, wherein $B_6$, $B_7$, $B_8$, and $B_9$ are each a carbon atom, $R^1$, $R^2$, $R^3$ and $R^4$ independently of one another are hydrogen atom, halogen, cyano, nitro, amino, —O—($C_1$–$C_7$)-alkyl, phenyl, —O-phenyl, —$CF_2$—$CF_3$, —$CF_3$, $N(R^{13})_2$, wherein $R^{13}$ is independently of one another chosen from hydrogen atom, —($C_1$–$C_7$)-alkyl, phenyl, —C(O)-phenyl, —C(O)-pyridyl, —C(O)—NH-phenyl, —C(O)—O-phenyl, —C(O)—O—($C_1$–$C_4$)-alkyl, —C(O)—($C_1$–$C_7$)-alkyl or —($C_1$–$C_{10}$)-alkyl, wherein alkyl, pyridyl or phenyl are unsubstituted or mono- to tri-substituted by substituents independently chosen from those as defined under 7.1 to 7.11, or $R^{13}$ together with nitrogen atom to which it is bonded form a heterocycle having 5 to 7 ring atoms, —$S(O)_y$—$R^{14}$, wherein y is zero, 1 or 2, and $R^{14}$ is —($C_1$–$C_{10}$)-alkyl, phenyl, which phenyl is unsubstituted or mono- to penta-substituted as defined for substituents under 7.1 to 7.11, amino or —$N(R^{13})_2$, wherein $R^{13}$ is as defined above, wherein alkyl is unsubstituted or mono- to tri-substituted independently of one another as defined under 7.1 to 7.11, or —C(O)—O—$R^{12}$, wherein $R^{12}$ is as defined as in 11, above, $R^6$, $R^7$ and $R^8$ independently of one another are hydrogen atom, methyl, amino, —$N(R^{13})_2$, wherein $R^{13}$ is as defined above, provided that at least one of $R^1$, $R^2$, $R^3$, $R^4$ and $R^8$ is not a hydrogen atom, and $R^5$ is as defined immediately above.

Moreover, examples include the use of compounds of formula II

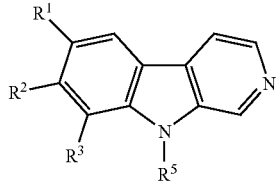

(II)

and/or a stereoisomeric form of the compounds of the formula II and/or a physiologically tolerable salt of the compounds of the formula II, for the production of pharmaceuticals for the prophylaxis and therapy of disorders in whose course an increased activity of $I_kB$ kinase is involved, wherein;

$R^1$, $R^2$ and $R^3$ are independently chosen from hydrogen atom, halogen, cyano, amino, —O—($C_1$–$C_4$)-alkyl, nitro, —$CF_3$, —$CF_2$—$CF_3$, —$S(O)_y$—$R^{14}$, wherein y is 1 or 2, $R^{14}$ is amino, —($C_1$–$C_7$)-alkyl, phenyl, which is unsubstituted or mono- to tri-substituted by substituents independently chosen from those as defined under 7.1 to 7.9, or —$N(R^{13})_2$, wherein $R^{13}$ is independently of one another chosen from —C(O)-pyridyl, hydrogen atom, —($C_1$–$C_7$)-alkyl-C(O)—($C_1$–$C_7$)-alkyl, —C(O)-phenyl, —($C_1$–$C_{10}$)-alkyl, —C(O)—NH—($C_1$–$C_4$)-alkyl, —C(O)—O-phenyl or —C(O)—O—($C_1$–$C_4$)-alkyl, wherein pyridyl, alkyl or phenyl are unsubstituted or mono- to tri-substituted independently of one another as defined under 7.1 to 7.11, or $R^{13}$ together with the nitrogen atom to which it is bonded form a heterocycle having 5 to 7 ring atoms, provided that at least one of $R^1$, $R^2$ and $R^3$ is not a hydrogen atom, and $R^5$ is hydrogen atom, —($C_1$–$C_{10}$)-alkyl, wherein alkyl is unsubstituted or mono- to tri-substituted by substituents independently chosen from those as defined under 7.1 to 7.4, —C(O)—$R^9$ or —$S(O)_2$—$R^9$, wherein $R^9$ is —($C_1$–$C_{10}$)-alkyl, —O—($C_1$–$C_{10}$)-alkyl, wherein alkyl is unsubstituted or mono- to tri-substituted by substituents independently chosen from those as defined under 7.1 to 7.4, phenyl, which is unsubstituted or mono- to tri-substituted by substituents independently chosen from those as defined under 7.1 to 7.11, or —$N(R^{13})_2$, wherein $R^{13}$ is as defined directly above.

Still further examples include the use of the compounds of formula II for the production of pharmaceuticals for the prophylaxis and therapy of disorders in whose course an increased activity of $I_kB$ kinase is involved, wherein $R^1$, $R^2$ and $R^3$ are independently chosen from hydrogen atom, halogen, cyano, amino, —O—($C_1$–$C_4$)-alkyl, nitro, —$CF_3$ or $N(R^{13})_2$, wherein $R^{13}$ is independently of one another chosen from hydrogen atom, —($C_1$–$C_7$)-alkyl, —C(O)—($C_1$–$C_7$)-alkyl, —C(O)-pyridyl, —C(O)-phenyl or —C(O)—O—($C_1$–$C_4$)-alkyl, wherein alkyl or phenyl are unsubstituted or mono- to tri-substituted by substituents independently chosen from halogen or —O—($C_1$–$C_4$)-alkyl, and $R^5$ is hydrogen atom, —C(O)—$CH_3$, methyl, —$S(O)_2$—$CH_3$, —C(O)-morpholinyl, —$CH_2$—$CH_2$—OH or —$CH_2$—C(O)—$NH_2$, provided that no more than two of $R^1$, $R^2$, $R^3$ and $R^5$ are a hydrogen atom.

Further examples include the use of compounds of formula II for the production of pharmaceuticals for the prophylaxis and therapy of disorders in whose course an increased activity of IkB kinase is involved, wherein $R^1$ is bromo, —$CF_3$ or chloro, $R^2$ is hydrogen atom or O—($C_1$–$C_2$)-alkyl, $R^3$ is hydrogen atom, bromo, chloro or —$N(R^{13})_2$, wherein $R^{13}$ is independently of one another chosen from hydrogen atom, —C(O)-phenyl, —($C_1$–$C_7$)-alkyl, —C(O)—($C_1$–$C_4$)-alkyl or —C(O)—O—($C_1$–$C_4$)-alkyl, wherein alkyl or phenyl are unsubstituted or mono- to tri-substituted by substituents independently chosen from halogen or —O—($C_1$–$C_2$)-alkyl, and $R^5$ is hydrogen atom, —C(O)—$CH_3$, methyl or —$S(O)_2$-$CH_3$, provided that no more than two of $R^1$, $R^2$, $R^3$ and $R^5$ are a hydrogen atom.

Specific examples include the use of the compounds of formula II for the production of pharmaceuticals for the prophylaxis and therapy of disorders in whose course an increased activity of IkB kinase is involved, wherein R¹ is chloro, R² and R³ are each hydrogen atom, and R⁵ is —C(O)—CH₃, or R¹ is bromo, R² and R³ are each hydrogen atom, and R⁵ is —C(O)—CH₃, or R¹ is chloro, R³ is —N—C(O)—CH₂—O—CH₃ and R² and R⁵ are each hydrogen atom, or R¹ is chloro, R³ is —N—C(O)-para-fluoro-phenyl and R² and R⁵ are each hydrogen atom, or R¹ and R³ are each chloro, R² is —C(O)—CH₃ and R⁵ is hydrogen atom, or R¹ and R³ are each chloro, R⁵ is hydrogen atom and R² is —C(O)—CH₂—CH₃.

On account of the pharmacological properties, the compounds according to the invention are suitable for the prophylaxis and therapy of all those disorders in whose course an increased activity of IkB kinase is involved. Disorders in whose course an increased activity of IkB kinase is involved include, for example the treatment of joint inflammation, including arthritis, rheumatoid arthritis and other arthritic conditions such as rheumatoid spondylitis, gouty arthritis, traumatic arthritis, rubella arthritis, psoriatic arthritis and osteoarthritis. Additionally, the compounds are useful in the treatment of acute synovitis, tuberculosis, atherosclerosis, muscle degeneration, cachexia, Reiter's syndrome, endotoxaemia, sepsis, septic shock, endotoxic shock, gram negative sepsis, gout, toxic shock syndrome, chronic pulmonary inflammatory diseases including. asthma and adult respiratory distress syndrome, silicosis, pulmonary sarcoidosis, bone resorption diseases, reperfusion injury, carcinoses, leukemia, sarcomas, lymph node tumors, skin carcinoses, lymphoma, apoptosis, graft. versus host reaction, allograft rejection and leprosy. Furthermore, the compounds are useful in the treatment of: infections such as viral infections, for example HIV, cytomegalovirus (CMV), influenza, adenovirus and the Herpes group of viruses, parasitic infections, for example malaria such as cerebral malaria, and yeast and fungal infections, for example fungal meningitis; fever and myalgias due to infection; AIDS; AIDS related complex (ARC); cachexia secondary to infection or malignancy; cachexia secondary to acquired immune deficiency syndrome (AIDS) or to cancer; keloid and scar tissue formation; pyresis; diabetes; and inflammatory bowel diseases such as Crohn's disease and ulcerative colitis. The compounds of the invention are also useful in the treatment of diseases of or injury to the brain in which over-expression of TNFα has been implicated such as multiple sclerosis, and head trauma. The compounds according to the invention are also useful in the treatment of psoriasis, Alzheimer's disease, carcinomatous disorders (potentiation of cytotoxic therapies), cardiac infarct, chronic obstructive pulmonary disease (COPD) and acute respiratory distress syndrome (ARDS).

The invention also relates to a process for the production of a pharmaceutical, which comprises bringing at least one compound of the formula I into a suitable administration form using a pharmaceutically suitable and physiologically tolerable excipient and, if appropriate, further suitable active compounds, additives or auxiliaries.

Suitable solid or pharmaceutical preparation forms are, for example, granules, powders, coated tablets, tablets, (micro)capsules, suppositories, syrups, juices, suspensions, emulsions, drops or injectable solutions, and preparations having protracted release of active compound, in whose preparation customary auxiliaries, such as excipients, disintegrants, binders, coating agents, swelling agents, glidants or lubricants, flavourings, sweeteners and solubilizers are used. Frequently used auxiliaries which may be mentioned are magnesium carbonate, titanium dioxide, lactose, mannitol and other sugars, talc, lactoprotein, gelatin, starch, cellulose and its derivatives, animal and vegetable oils such as cod liver oil, sunflower, groundnut or sesame oil, polyethylene glycol and solvents such as, for example, sterile water and mono- or polyhydric alcohols such as glycerol.

The pharmaceutical preparations may be produced and administered in dose units, each unit containing as active constituent a certain dose of the compound of the formula I according to the invention. In the case of solid dose units such as tablets, capsules, coated tablets or suppositories, this dose can be up to approximately 1000 mg, such as from approximately 50 mg to 300 mg and in the case of injection solutions in ampoule form up to approximately 300 mg, such as from approximately 10 mg to 100 mg.

For the treatment of an adult patient weighing approximately 70 kg, depending on the efficacy of the compound according to formula I, daily doses of approximately 20 mg to 1000 mg of active compound, such as from approximately 100 mg to 500 mg, are indicated. Under certain circumstances, however, even higher or lower daily doses may be appropriate. The administration of the daily dose can be carried out both by single administration in the form of an individual dose unit or else of a number of smaller dose units and by multiple administration of subdivided doses at specific intervals.

As a rule, final products are determined by mass-spectroscopic methods (FAB-, ESI-MS). Temperatures are given in degrees Celsius, RT means room temperature (22° C. to 26° C.). Abbreviations used are either explained or correspond to the customary conventions.

The following examples are numbered so as to correspond to the compounds of Table 1, below.

EXAMPLE 1

7-bromo-β-carboline

A solution of norharmane (600 mg, 3.57 mmol) in tetrahydrofuran (THF; 50 ml) was treated with bromine (0.40 ml, 7.80 mmol) at RT while stirring. After stirring for 18 h at RT, the reaction was concentrated under reduced pressure and the resulting residue was sonicated in 10% aqueous Na₂CO₃ (100 ml). The product was filtered and washed with water to give 905 mg of crude product. The crude product was crystallized from xylenes to provide in two crops 580 mg of 7-bromo-β-carboline.

EXAMPLE 2

1-acetyl-7-bromo-β-carboline

A solution of Example 1 (25 mg, 0.1 mmol) in dimetylformamide (DMF; 2 ml) was treated with 0.10 ml of 1 M aqueous NaOH (0.10 mmol). After stirring at RT for 30 minutes, acetic anhydride (0.010 ml, 0.095 mmol) was added and reaction stirred 18 h at RT. The reaction was partitioned in EtOAc and 5% citric acid and the organic layer washed with water, dried (brine; MgSO₄), and concentrated to give 23 mg of crude product. The crude product was chromatographed (7:3 hexane-acetone) on silica gel to give 10 mg of 1-acetyl-7-bromo-β-carboline.

EXAMPLE 3

7-fluoro-β-carboline

A mixture of 5-fluorotryptamine hydrochloride (200 mg, 0.93 mmol) in EtOAc (4 ml) and water (2 ml) was treated with glyoxalic acid hydrate (90 mg, 0.98 mmol). The pH of the aqueous layer was adjusted to 5 (with 5% NaHCO$_3$ then 1M HCl) and the mixture stirred vigorously at RT for 18 h. The mixture was then diluted with hexane (4 ml) and the product filtered and washed with water and (1:1) hexane-ethyl acetate.

The crude product from above in 6N HCl (3 ml) was treated 3 times with concentrated HCl (0.050 ml) every 15 min while refluxing. After refluxing for a total of 45 min, the reaction was concentrated to give a residue. The above residue was slurred in xylenes with triethylamine (0.40 ml, 2.9 mmol) and 10% Pd/C (200 mg). The mixture was refluxed for 1 h and then filtered hot through celite. The filtrate was concentrated and the residue chromatographed (5:95 methanol-chloroform) on silica gel to give 25 mg of 7-fluoro-β-carboline.

EXAMPLE 4

7-isopropyl-β-carboline hydrochloride

A mixture of 4-isopropylphenylhydrazine hydrochloride (660 mg, 3.55 mmol) and 4-phthalimidobutanal diethyl acetal (1.15 g, 3.95 mmol) in Ethanol (EtOH; 30 ml) was heated at 60° C. to 65° C. for 1 h with water (0.050 ml). The mixture was then treated with concentrated HCl (0.50 ml) and refluxed for 14 h. After concentrating the reaction, the residue was partioned in methylene chloride and saturated aqueous NaHCO$_3$. The aqueous solution was extracted with methylene chloride (3 times) and the combined organic solutions were dried (MgSO$_4$) and concentrated to give after chromatography (4:1 hexane-ethyl acetate) on silica gel 146 mg of product. The above product was treated with hydrazine hydrate (1 ml) in EtOH (4 ml) and water (1 ml) and stirred at RT overnight. After concentrating the reaction to an aqueous mixture, the product was extracted with methylene chloride (3 times). The combined organic solution was dried (MgSO$_4$) and concentrated. The residue was redissolved in methylene chloride and treated with 1M HCl in ether. The precipitate was collected and washed with ether and hexane and dried to provide 102 mg of 6-isopropyl-tryptamine hydrochloride salt. This tryptamine obtained above was transformed into 7-isopropyl-β-carboline according to the procedure used in example 3. The hydrochloride salt was obtained by treating a solution of 7-Isopropyl-β-carboline in methylene chloride with 1M HCl in ether and concentrating. The residue was triturated with (1:1) methylene chloride-hexane to give 15 mg of 7-isopropyl-β-carboline hydrochloride.

EXAMPLE 5

7-cyano-β-carboline

A dark solution of example 1 (190 mg, 0.62 mmol) and CuCN (110 mg, 1.22 mmol) in N-methyl 2-pyrrolidone (1.5 ml) was heated in a sealed reaction tube at 200° C. for 48 h. The mixture was filtered and the filtrate was diluted with water (50 ml). A brown solid that precipitated was filtered, washed with water, saturated aqueous NaHCO$_3$, and then methanol. This material was dissolved in DMSO and diluted with aqueous HCl. This homogeneous dark solution was decolorized with charcoal, filtered and concentrated to give a concentrated solution in DMSO. This DMSO solution was partitioned in (1:1) EtOAc-THF and saturated aqueous NaHCO$_3$. The organic solution was dried (MgSO$_4$) and concentrate to give 8 mg of 7-cyano-β-carboline.

EXAMPLE 6

7-nitro-β-carboline Hydrochloride

Norharmane (100 mg, 0.60 mmol) was treated with concentrated nitric acid (1.0 ml) and the resulting suspension was heated to 65° C. until the mixture became homogeneous (3 to 4 min). The solution was carefully poured into water (20 ml), and the precipitate filtered and washed with water then methanol. The solid was suspended in saturated aqueous NaHCO$_3$ and stirred vigorously before filtering and washing with water. The solid was taken up in hot methanol and this solution treated with 1M HCl in ether (5 ml). The solution was concentrated and the residue triturated with ether to provide 58 mg of a 7:3 mixture of 7-nitro-β-carboline hydrochloride and 9-nitro-β-carboline hydrochloride.

EXAMPLE 7

7-carboxy-β-carboline Trifluoroacetat

Crude product from example 5 (from 210 mg of example 1, 0.85 mmol) was treated with 6 M HCl in a sealed reaction tube for 15 h at 110° C. The reaction was evaporated to give a concentrated solution of product in N-methyl 2-pyrrolidone. A portion (half) was purified by preparative HPLC using a C$_{18}$-packed column and eluting with a gradient (5:95 to 50:50) of water-acetonitril (with 0.1% trifluoracetic acid). The pure fractions were combined and lyophilized to provide 11 mg of 7-carboxy-β-carboline trifluoroacetate.

EXAMPLE 8

7,9-dibromo-β-carboline Hydrochloride

A solution of the product from example 1 (140 mg, 0.58 mmol) in THF (2 ml) was treated with bromine (0.50 ml). After 10 min at RT, the reaction was diluted with chloroform and the product was filtered. The filtered product was taken up in methanol and treated with 1M HCl in ether and concentrated. The residue was triturated with ether to provide 160 mg of 7,9-dibromo-β-carboline hydrochloride.

EXAMPLE 9

7,9-dichloro-β-carboline

To a suspension of norharmane (84 mg, 0.50 mmol) in water (3 ml) at RT was added 1M aqueous HCl (1.1 ml, 1.1 mmol). To this homogenous solution was added N-chlorosuccinimide (747 mg, 5.58 mmol) portionwise and the resulting solution was stirred at 60° C. to 70° C. for 3 h. The reaction was partitioned in EtOAc and saturated aqueous NaHCO$_3$ and the organic layer was dried (brine; MgSO$_4$) and then concentrated. The residue was chromatographed (2:3 THF-hexane) on silica gel to give 24 mg of 7,9-dichloro-β-carboline after triturating with (1:1) methylene chloride-hexane, then with hexane.

EXAMPLE 10

1-acetyl-7-bromo-β-carboline

To a suspension of NaH (95%, 14 mg, 0.60 mmol) in DMF (1.0 ml) at 5° C. to 10° C. was added the product from example 1 (74 mg, 0.30 mmol). The resulting mixture was stirred for 15 min at 5° C. to 10° C. before adding methanesulfonylchloride (0.030 ml, 0.38 mmol). The reaction was allowed to warm to RT and stirred for 2 h before partitioning into saturated aqueous NaHCO$_3$ and EtOAc. After stirring the mixture overnight, the organic layer was washed with water, dried (brine; MgSO$_4$), and concentrated. The residue was purified by chromatography (1:1 hexane-ethyl acetate) on silica gel to give, 23 mg of 1-acetyl-7-bromo-β-carboline.

EXAMPLE 11

7-bromo-1-methyl-β-carboline

To a suspension of NaH (95%, 6 mg, 0.24 mmol) in DMF (2.0 ml) at 5° C. to 10° C. was added the product from example 1 (50 mg, 0.20 mmol). The resulting mixture was stirred for 15 min at 5° C. to 10° C. before adding methyliodide (0.030 ml, 0.20 mmol) at 0° C. to 5° C. The reaction was stirred for 12 h at 0° C. to 5° C. before partitioning into water and EtOAc. The organic layer was washed with water, dried (brine; MgSO$_4$), and concentrated. The residue was purified by chromatography (gradient, 1:3 hexane-ethyl acetate to ethyl acetate) on silica gel to give 10 mg of 7-bromo-1-metyhl-β-carboline.

EXAMPLE 12

7-chloro-β-carboline

To a solution of norharmane (2.0 g, 11.9 mmol) in water (89 ml) and 1M aqueous HCl (29.8 ml, 29.8 mmol) was added N-chlorosuccinimide (3.17 g, 23.8 mmol) portionwise. The resulting solution was stirred at RT for 6 h, and then at 0° C. to 5° C. for 12 h. The reaction was diluted with water (100 ml) and basified cautiously with solid K$_2$CO$_3$ (4.3 g). After stirring at RT for 1 h, the product was collected and washed with water. The crude product was refluxed in chloroform for 1 h and filtered after cooling to 15° C. to provide 2.05 g of 7-chloro-β-carboline.

EXAMPLE 13

1-acetyl-7-chloro-β-carboline

To a solution of the product from example 12 (104 mg, 0.50 mmol) in DMF (2.0 ml) at 3° C. to 5° C. was added NaH (95%, 15 mg, 0.625 mmol). The resulting mixture was stirred for 15 min before adding acetic anhydride (0.083 ml, 0.875 mmol). The reaction was allowed to warm to RT and stirred for 3 h before pouring into with water (25 ml). The slurry was stirred for 12 h, and the product collected to give after chromatography (1:3 hexane-ethyl acetate) on silica gel 82 mg of 1-acetyl-7-chloro-β-carboline.

EXAMPLE 14

7-chloro-9-nitro-β-carboline

A mixture of the product from example 12 (500 mg, 2.48 mmol) in concentrated nitric acid (20 ml) was stirred at RT for 22 h. The reaction mixture was carefully poured into cold (3° C. to 5° C.) water (50 ml), and after stirring for 2 h the precipitate was collected. The solid was suspended in saturated aqueous NaHCO$_3$ (50 ml) and stirred at RT for 12 h. The product was filtered and washed with water to provide 550 mg of 7-chloro-9-nitro-β-carboline

EXAMPLE 15

9-amino-7-chloro-β-carboline

To a suspension of the product from example 14 (548 mg, 2.22 mmol) in EtOH (14 ml) at 65° C. to 70° C. was added tin chloride dihydrate (2.5 g, 11.1 mmol). Thereafter, 6M aqueous HCl (14 ml) was added dropwise. The mixture was stirred at 70° C. to 80° C. for 3.5 h and then partitioned slowly into saturated aqueous NaHCO$_3$ (150 ml) and EtOAc (100 ml). The aqueous phase was extracted (2 times) and the combined organic solutions dried (brine; NaSO$_4$) and concentrated to give 484 mg of 9-amino-7-chloro-β-carboline.

EXAMPLE 16

9-amino-7-chloro-β-carboline Trifuoroacetate

To a solution of the product from example 15 (35 mg, 0.16 mmol) in pyridine (0.80 ml) was added acetic anhydride (0.018 ml, 0.19 mmol). The resulting mixture was allowed to stand at RT for 12 h before pouring into water (15 ml). The crude product was filtered and purified by preparative HPLC using a C$_{18}$-packed column and eluting with a gradient (5:95 to 60:40) of water-acetonitril (with 0.1% trifluoracetic acid). The pure fractions were combined and lyophilized to provide 18 mg of 9-amino-7-chloro-β-carboline trifluoroacetate.

EXAMPLE 17

7-bromo-1-carbonyl-(4'-morpholine)-β-carboline

A solution of the product from example 1 (125 mg, 0.51 mmol) in DMF (2 ml) was treated with 0.55 ml of 1M aqueous NaOH (0.55 mmol). After stirring at RT for 30 minutes, 4-morpholinecarbonyl chloride (0.060 ml, 0.51 mmol) was added and reaction stirred 18 h at RT. The reaction was partitioned in EtOAc and 5% citric acid and the organic layer washed with water, dried (brine; MgSO$_4$), and concentrated. The residue was chromatographed (7:3 hexane-acetone) on silica gel to give 105 mg of 7-bromo-1-carbonyl-(4'-morpholino)-β-carboline.

EXAMPLE 18

1-(2'-ethylacetate)-7-chloro-β-carboline

To a suspension of NaH (95%, 28 mg, 1.15 mmol) in DMF (1.0 ml) at 5° C. to 10° C. was added the product from example 12 (202 mg, 1.0 mmol) in DMF (3 ml). The resulting mixture was stirred for 30 min at 5° C. to 10° C. before adding ethyl bromoacetate (0.116 ml, 1.05 mmol). The reaction was allowed to be stirred for 1.5 h and then the reaction was diluted with saturated aqueous NaHCO₃ (30 ml). The product was extracted with EtOAc (30 ml; 2 times each 15 ml), and the combined organic extracts were dried (brine; MgSO₄) then concentrated. The residue was purified by chromatography (1:3 hexane-ethyl acetate) on silica gel to give 270 mg of 1-(2'ethylacetate)-7-chloro-β-carboline.

EXAMPLE 19

1-(2'-ethanoyl)-7-chloro-β-carboline

To a solution of the product from example 18 (50 mg, 0.17 mmol) in THF (1.7 ml) at 5° C. to 10° C. was added 1M LAH in THF (0.17 ml, 0.17 mmol). The resulting mixture was stirred for 2 h at 5° C. to 10° C. before adding EtOAc (0.10 ml). The mixture was subsequently diluted with EtOAc (5 ml) and slowly treated with saturated aqueous NaHCO3 (5 ml). After diluting with water (10 ml) and brine (10 ml) the mixture was extracted with EtOAc. The organic solution was dried (brine; MgSO₄) then concentrated to give 42 mg of 1-(2'ethanol)-7-chloro-β-carboline.

EXAMPLE 20

1-(2'-acetyl)-7-chloro-β-carboline

To a solution of the product from example 18 (107 mg, 0.37 mmol) in MeOH (3.7 ml) at RT was added water (3.7 ml) followed by treatment with 1M aqueous NaOH (0.41 ml, 0.41 mmol). The resulting mixture was stirred for 2 h and the volatile removed under reduced pressure. The mixture was subsequently diluted with water (5 ml) and the pH adjusted to 5 to 6. The precipitate was filtered and washed with water to give 96 mg of 1-(2'-acetyl)-7-chloro-β-carboline.

EXAMPLE 21

8-methoxy-β-carboline

Prepared from 6-methoxytryptamine using the procedure as in example 3.

EXAMPLE 22

See Table 1 for Structure

To a solution of the product from example 20 (59 mg, 0.23 mmol) in DMF (2.8 ml) at RT was added p-nitrophenol (40 mg, 0.29 mmol) followed by 1-ethyl-3-(3-dimethylaminopropyl)carbodiimide (48 mg, 0.25 mmol). The resulting mixture was stirred for 1.5 h at RT and then ammonium bicarbonate (55 mg, 0.69 mmol) was added. The reaction was stirred for 18 h at RT and then poured into water (20 ml). The aqueous mixture was basified to pH of about 10 with K₂CO₃. The precipitate was filtered and washed with water to give 47 mg of the title compound.

EXAMPLE 23

8-hydroxy-2-methyl-β-carboline

A solution of harmine (616 mg, 2.9 mmol) in dichloroethane (20 ml) was treated with 2.0 ml of 1M BBr₃ (4 mmol) in dichloroethane. The reaction was stirred at 60° C. for 48 h and then cooled to 0° C. before quenching with MeOH (5 ml). The reaction was concentrated and the residue triturated with methanol to give 413 mg of 8-hydroxy-2-methyl-β-carboline.

EXAMPLE 24

6,8-dibromo-7-methoxy-β-carboline

A solution of the product from example 30 (90 mg, 0.45 mmol) in acetic acid (8 ml) was treated with bromine (0.025 ml, 0.48 mmol). The reaction was stirred at RT for 18 h and then concentrated. The residue was partitioned in EtOAc and aqueous NaHCO₃. The organic layer was dried (brine; MgSO₄) and concentrated. The residue was purified by chromatography (5:4 hexane-acetone) on silica gel to give 3 mg of 6,8-dibromo-7-methoxy-β-carboline.

EXAMPLE 25

See Table 1 for Structure

A solution of the product from example 23 (60 mg, 0.30 mmol) in DMF (3 ml) was treated with K₂CO₃ (100 mg) and t-butyl bromoacetate (0,040 ml, 0.27 mmol). After stirring at RT for 18 h, the reaction was partitioned in EtOAc and water. The organic layer was dried (brine; MgSO₄) and then concentrated. The residue was chromatographed (1:1 hexane-EtOAc) on silica gel to give 20 mg of the title compound.

EXAMPLE 26

See Table for Structure

A solution of the product from example 23 (50 mg, 0.25 mmol) in DMF (3 ml) was treated with K₂CO₃ (100 mg) and benzyl bromide (0,030 ml, 0.25 mmol). After stirring at RT for 18 h, the reaction was partitioned in EtOAc and water. The organic layer was dried (brine; MgSO₄) and then concentrated. The residue was chromatographed (1:1 hexane-EtOAc) on silica gel to give 12 mg of the title compound.

EXAMPLE 27

7-ethoxy-2-methyl-β-carboline

A solution of the product from example 23 (60 mg, 0.30 mmol) in DMF (3 ml) was treated with K₂CO₃ (100 mg) and ethyl iodide (0,029 ml, 0.36 mmol). After stirring at RT for 18 h, the reaction was partitioned in EtOAc and water. The organic layer was dried (brine; MgSO₄) and then concentrated. The residue was chromatographed (1:1 hexane-acetone) on silica gel to give 20 mg of 7-ethoxy-2-methyl-β-carboline.

EXAMPLE 28

7-bromo-2-methyl-β-carboline

Prepared from harmane using the same procedure as in example 1.

EXAMPLE 29

See Table 1 for Structure

A solution of the product from example 23 (60 mg, 0.30 mmol) in DMF (3 ml) was treated with K₂CO₃ (100 mg) and acetic anhydride (0,034 ml, 0.36 mmol). After stirring at RT for 18 h, the reaction was partitioned in EtOAc and water. The organic layer was dried (brine; MgSO₄) and then concentrated. The residue was chromatographed (1:1 hexane-acetone) on silica gel to give 18 mg of the title compound.

EXAMPLE 30

7-methoxy-β-carboline

Prepared from 5-methoxytryptamine using the procedure in example 3.

EXAMPLE 31

8-fluoro-β-carboline

Prepared from 6-fluorotryptamine using the same procedure as in example 3.

EXAMPLE 32

7-bromo-2-methyl-8-methoxy-β-carboline

Prepared from harmine using the same procedure as in example 1.

EXAMPLE 33

7-hydroxy-β-carboline

Prepared from the product of example 30 using the procedure in example 23.

EXAMPLE 34

7-chloro-8-fluoro-β-carboline

Prepared from the product of example 31 using the procedure in example 12.

EXAMPLE 35

7-methoxy-1-methyl-β-carboline

Prepared from the product of example 30 using the procedure in example 11.

EXAMPLE 36

9-chloro-8-methoxy-β-carboline Trifluoroacetate and

EXAMPLE 37

7,9-dichloro-8-methoxy-β-carboline Trifluoroacetate

A solution of the product from example 21 (195 mg, 1.0 mmol) in 1M HCl (3 ml) was treated with N-chlorosuccinimide (270 mg, 2 mmol) portionwise and the resulting solution was stirred at 60° C. to 70° C. for 3 h. The reaction was evaporated and the crude product purified by preparative HPLC using a $C_{18}$-packed column and eluting with a gradient (5:95 to 50:50) of water-acetonitril (with 0.1% trifluoroacetic acid). The pure fractions of each product were combined and lyophilized to provide 78 mg of 9-chloro-8-methoxy-β-carboline trifluoroacetate and 51 mg of 7,9-dichloro-8-methoxy-β-carboline trifluoroacetate.

EXAMPLE 38

7,9-dichloro-8-hydroxy-β-carboline

A mixture of the product of example 37 (590 mg, 2.21 mmol) in methylene chloride (25 ml) at 35° C. was treated with a solution of $BBr_3$ in methylene chloride (1M, 6 ml, 6 mmol). After refluxing for 3 h, the reaction was quenched with methanol (5 ml) and then concentrated. The residue was slurred in 60% $NaHCO_3$ solution, the product filtered and washed with water to give 500 mg of 7,9-dichloro-8-hydroxy-β-carboline.

EXAMPLE 39

7,9-dichloro-8-ethoxy-β-carboline

A mixture of the product of example 38 (35 mg, 0.14 mmol), $K_2CO_3$ (100 mg), and ethyl iodide (0.014 ml, 0.17 mmol) in acetone (5 ml) was stirred in a closed reaction tube at RT for 3 days. After concentrating the reaction, the residue was partitioned in ethyl acetate and water. The organic layer was dried (MgSO4) and concentrated to give crude product. The crude product was chromatographed (5% methanol in chloroform) on silica gel to give 8 mg of 7,9-dichloro-8-ethoxy-β-carboline.

EXAMPLE 40

7-chloro-8-fluoro-β-carboline trifluoroacetate

A solution of the product of example 31 (78 mg, 0.42 mmol) in 1M HCl (1 ml) was treated with N-chlorosuccinimide (115 mg, 0.9 mmol) portionwise and the resulting mixture was stirred at 60° C. to 70° C. for 3 h. The reaction was evaporated and the crude product purified by preparative HPLC using a $C_{18}$-packed column and eluting with a gradient (5:95 to 50:50) of water-acetonitril (with 0.1% trifluoroacetic acid). The pure fractions with product were combined and lyophilized to provide 33 mg of the title compound.

EXAMPLE 41

1-hydroxy-7-trifluoromethyl-β-carboline and

EXAMPLE 42

7-tri-fluoromethyl-β-carboline

A solution of 3-hydroxy-2-piperdone (96 mg, 0.83 mmol) in methylene chloride (5 ml) was treated with Dess Martin reagent (352 mg, 0.85 mmol) at RT and the resulting mixture was stirred for 1 h. After filtering the salts from the reaction, the ketone in solution was treated with 4-trifluoromethyl-phenyl-hydrazine (145 mg, 0.83 mmol). After 15 min, hexane (20 ml) was added and the hydrazone collected by filtration. This crude hydrazone was heated at 95° C. in formic acid (70%, 10 ml) for 1 h. The reaction was evaporated and the residue was chromatographed (ethyl acetate) on silica gel to give 60 mg of dihydro 1-hydroxy-7-trifluoromethyl-β-carboline.

A portion of dihydro 1-hydroxy-7-trifluoromethyl-β-carboline (6 mg) in xylenes (1 ml) was treated with Pd/C (10%, 7 mg) and the mixture heated at 50° C. for one week. The reaction was concentrated after filtering it through celite, and the residue was chromatographed (1:1 hexane-ethyl acetate) on silica gel to give 1 mg of 1-hydroxy-7-trifluoromethyl-β-carboline. A portion of dihydro 1-hydroxy-7-trifluoromethyl-β-carboline (25 mg) in THF (1 ml) was treated with a solution of lithium aluminum hydride in THF (1 M, 0.5 ml). The reaction was stirred at 60° C. for 6h before quenching with water (5 ml) and extracting with ethyl acetate (3 times 10 ml). The combined organic layers were dried ($MgSO_4$) and concentrated to provide tetrahydro 7-trifluoro-methyl-β-carboline. This material was taken up in xylenes (5 ml) and treated with Pd/C (10%, 15 mg). The mixture was stirred at 150° C. for 48 h before filtering through celite and concentrating. The residue was chromatographed (ethyl acetate) on silica gel to give 5 mg of 7-tri-fluoromethyl-β-carboline.

EXAMPLE 43

7-chloro-9-(methylamino)-β-carboline Trifluoroacetate

A solution of the product of example 15 (50 mg, 0.23 mmol) in AcOH/methanol (1%, 3 ml) was treated with sodium cyanoborohydride (30 mg, 0.46 mmol) followed by formaldehyde (37%, 0.017 ml, 0.23 mmol). The reaction was stirred at RT for 36 h and then diluted with saturated $NaHCO_3$ (9 ml). After stirring for 15 min, the crude product was filtered and washed with water. The crude product was purified as described in example 46. The pure fractions with product were combined and lyophilized to provide 13 mg of the title compound.

EXAMPLE 44

7-chloro-9-(dimethylamino)-β-carboline trifluoroacetate

A solution of the product of example 15 (50 mg, 0.23 mmol) in AcOH/methanol (1%, 3 ml) was treated with sodium cyanoborohydride (30 mg, 0.46 mmol) followed by formaldehyde (37%, 0.060 ml, 0.69 mmol). The reaction was stirred at RT for 36 h and then diluted with saturated $NaHCO_3$ (9 ml). After stirring for 15 min, the crude product was filtered and washed with water. The crude product was purified as described in example 46. The pure fractions with product were combined and lyophilized to provide 40 mg of the title compound.

EXAMPLE 45

7-chloro-9-(methylsulfonylamino)-β-carboline Trifluoroacetate

A solution of the product of example 15 (30 mg, 0.14 mmol) in pyridine (0.5 ml) was treated with methanesulfonyl chloride (0.024 ml, 0.30 mmol) in two portions over 30 h. The reaction was diluted with water (5 ml) and the crude product collected and washed with water (several times). The crude product was purified as described in example 46. The pure fractions with product were combined and lyophilized to provide 16 mg of the title compound.

EXAMPLE 46

7-chloro-9-(propyionylamino)-β-carboline trifluoroacetate

A solution of the product of example 15 (30 mg, 0.14 mmol) in pyridine (1.0 ml) was treated with propionyl chloride (0.015 ml, 0.17 mmol). After stirring at RT for 4 h, the reaction was diluted with water (9 ml) and saturated $NaHCO_3$ (1 ml). The crude product was collected and washed with water (several times). The crude product was purified by preparative HPLC using a $C_{18}$-packed column and eluting with a gradient (5:95 to 50:50) of water-acetonitril (with 0.1% trifluoroacetic acid). The pure fractions with product were combined and lyophilized to provide 21 mg of the title compound.

EXAMPLE 47

7-chloro-9-(benzoylamino)-β-carboline Trifluoroacetate

A solution of the product of example 15 (30 mg, 0.14 mmol) in pyridine (1.0 ml) was treated with benzoyl chloride (0.020 ml, 0.17 mmol). After stirring at RT for 4 h, the reaction was diluted with water (9 ml) and saturated $NaHCO_3$ (1 ml). The crude product was collected and washed with water (several times). The crude product was purified as described in example 46. The pure fractions with product were combined and lyophilized to provide 12 mg of 7-chloro-9-(benzoylamino)-β-carboline trifluoroacetate.

EXAMPLE 48

7-chloro-9-(Acetyl-methylamino)-β-carboline Trifluoroacetate

A solution of the product of example 43 (19 mg, 0.082 mmol) in pyridine (0.40 ml) was treated with acetic anhydride (0.037 ml, 0.36 mmol) in two portions over 48 h. The reaction was subsequently concentrated to dryness and the residue coevaporated with AcOH under reduced pressure. The crude product was purified as described in example 46. The pure fractions with product were combined and lyophilized to provide 9 mg of the title compound.

EXAMPLE 49

7-chloro-9-(4-fluorobenzoylamino)-β-carboline Trifluoroacetate

A solution of the product of example 15 (30 mg, 0.14 mmol) in pyridine (1.0 ml) was treated with 4-fluorobenzoyl chloride (0.018 ml, 0.17 mmol). After stirring at RT for 18 h, the reaction was diluted with water (10 ml). The crude product was purified as described in example 46. The pure fractions with product were combined and lyophilized to provide 13 mg of the title compound.

EXAMPLE 50

A cold (3° C. to 5° C.) solution of the product of example 15 (30 mg, 0.14 mmol) and pyridine (0.014 ml, 0.17 mmol) in THF (0.7 ml) was treated with phenyl chloroformate (0.018 ml, 0.145 mmol). After stirring at RT for 2 h, the reaction was partitioned in ethyl acetate and buffer (pH 7.2). The organic layer was dried (brine, Na2SO$_4$) and concentrated to give 43 mg of phenyl carbamate.

To a solution of phenyl carbamate (30 mg, 0.089 mmol) in DMSO (0.5 ml) was added 2-methoxyethylamine (0.010 ml, 0.10 mmol). After stirring at RT for 30 min, the crude reaction mixture was purified as described in example 46. The pure fractions with product were combined and lyophilized to provide 21 mg of the title compound.

EXAMPLE 51

7-chloro-9-(methoxyacetylamino)-β-carboline Trifluoroacetate

A solution of the product of example 15 (35 mg, 0.16 mmol) in pyridine (1.0 ml) was treated with methoxyacetyl chloride (0.016 ml, 0.18 mmol). After stirring at RT for 2 h, the reaction was diluted with water (10 ml). The crude product was purified as described in example 46. The pure fractions with product were combined and lyophilized to provide 32 mg of the title compound.

EXAMPLE 52

7-chloro-9-(3-methoxybenzoxylamino)-β-carboline Trifluoroacetate

A solution of the product of example 15 (30 mg, 0.14 mmol) in pyridine (1.0 ml) was treated with m-anisoyl chloride (0.027 ml, 0.19 mmol) in two portions over 6 h. The reaction was subsequently diluted with water (10 ml) and the crude product was purified as described in example 46. The pure fractions with product were combined and lyophilized to provide 33 mg of the title compound.

EXAMPLE 53

7-chloro-9-(4-methoxybenzoxylamino)-β-carboline Trifluoroacetate

A solution of the product of example 15 (30 mg, 0.14 mmol) in pyridine (1.0 ml) was treated with p-anisoyl chloride (37 mg, 0.22 mmol) in two portions over 24 h. The reaction was subsequently diluted with water (10 ml) and the crude product was purified as described in example 46. The pure fractions with product were combined and lyophilized to provide 24 mg of the title compound.

EXAMPLE 54

7-chloro-9-(methylcarbamylamino)-β-carboline Trifluoroacetate

A solution of the product of example 15 (30 mg, 0.14 mmol) in pyridine (1.0 ml) was treated with p-anisoyl chloride (0.017 ml, 0.21 mmol) in two portions over 4 h. The reaction was subsequently diluted with water (10 ml) and the crude product was purified as described in example 46. The pure fractions with product were combined and lyophilized to provide 35 mg of the title compound.

EXAMPLE 55

7-chloro-9-(isovalerylamino)-β-carboline Trifluoroacetate

A solution of the product of example 15 (35 mg, 0.16 mmol) in pyridine (1.0 ml) was treated with isovalerylchloride (0.033 ml, 0.28 mmol) in two portions over 24 h. The reaction was subsequently diluted with water (10 ml) and the crude product was purified as described in example 46. The pure fractions with product were combined and lyophilized to provide 52 mg of the title compound.

EXAMPLE 60

N-(6-Chloro-9H-β-carbolin-8-yl)-nicotinamide

To a solution of norharmane (2.0 g, 11.9 mmol) in water (89 ml) and 1M aqueous HCl (29.8 ml, 29.8 mmol) was added N-chlorosuccinimide (3.17 g, 23.8 mmol) portionwise. The resulting solution was stirred at RT for 6 h, and then at 0° C. to 5° C. for 12 h. The reaction was diluted with water (100 ml) and basified cautiously with solid K$_2$CO$_3$ (4.3 g). After stirring at RT for 1 h, the product was collected and washed with water. The crude product was refluxed in chloroform for 1 h and filtered after cooling to 15° C. to provide 2.05 g of 7-chloro-β-carboline.

A mixture 7-chloro-β-carboline (500 mg, 2.48 mmol) in concentrated nitric acid (20 ml) was stirred at RT for 22 h. The reaction mixture was carefully poured into cold (3° C. to 5° C.) water (50 ml), and after stirring for 2 h the precipitate was collected. The solid was suspended in saturated aqueous NaHCO$_3$ (50 ml) and stirred at RT for 12 h. The product was filtered and washed with water to provide 550 mg of 7-chloro-9-nitro-β-carboline.

To a suspension of 7-chloro-9-nitro-β-carboline (548 mg, 2.22 mmol) in EtOH (14 ml) at 65° C. to 70° C. was added tin chloride dihydrate (2.5 g, 11.1 mmol). Thereafter, 6M aqueous HCl (14 ml) was added dropwise. The mixture was stirred at 70° C. to 80° C. for 3.5 h and then partitioned slowly into saturated aqueous NaHCO$_3$ (150 ml) and EtOAc (100 ml). The aqueous phase was extracted (2 times) and the combined organic solutions dried (brine; NaSO$_4$) and concentrated to give 484 mg of 9-amino-7-chloro-β-carboline.

To a cold (3–5° C.) solution of 9-amino-7-chloro-β-carboline (2.75 g, 12.7 mmol) in pyridine (150 ml) was added nicotinyl chloride hydrochloride (2.82 g, 15.8 mmol). The reaction was allowed to warm to RT and stirred for 20 h before diluting the reaction with water (100 ml) and 1M NaOH (25 ml). After stirring for 1 h at RT, the mixture was poured into water (200 ml). The mixture was allowed to stand for 1 h and the product was filtered to provide 3.80 g of the title compound after washing with water and drying under reduced pressure at RT.

EXAMPLE 68

N-(6-Chloro-7-methoxy-9H-β-carbolin-8-yl)-nicotinamide

A mixture of 6-methoxytryptamine (9.10 g, 47.8 mmol) in EtOAc (40 ml) and pH 4.5 NaOAc buffer (40 ml) was treated with glyoxalic acid hydrate (5.30, 57.6 mmol). The mixture was stirred vigorously for 2 days and then diluted with hexane (40 ml). The product was filtered and washed with water and (1:1) hexane-ethyl acetate. The crude product was crystallized from methanol after filtration of a hot methanol solution.

The crude product (11.5 g) from above in 6N HCl (100 ml) was treated 3 times with concentrated HCl (5.0 ml) every 15 min while refluxing. After refluxing for a total of 1 h, the reaction was concentrated to give a residue. This residue was slurried and sionicated with 10% $Na_2CO_3$ (300 ml) and filtered to give the free amine (7.20 g). The above amine was refluxed in xylenes (200 ml) and pyridine (100 ml) with 10% Pd/C (3 g) for 5 h. The hot reaction was filtered thru celite and the filtrate was concentrated to give 6.38 g of 8-methoxy-β-carboline.

To a mixture of 8-methoxy-β-carboline (1.0 g, 5 mmol) in THF (100 ml) was added N-chlorosuccinimide (0.70 g, 5.2 mmol). The reaction was stirred at RT for 4 h before concentrating and washing the residue with 1:1:1 mixture of 10% $Na_2CO_3$, hexane, and EtOAc (400 ml). The resulting residue was triturated with xylenes to provide 677 mg of 7-chloro-8-methoxy-β-carboline.

A solution of 7-chloro-8-methoxy-β-carboline (677 mg, 2.9 mmol) in trifluoroacetic acid (10 ml) was treated with $NaNO_3$ (260 mg, 3.06 mmol). The reaction was stirred for 3 h at RT and then concentrated. The crude product was chromatographed on silica eluting with a 5% to 10% methanol in chloroform gradient to provide 463 mg of 7-chloro-8-methoxy-9-nitro-β-carboline.

A solution of 7-chloro-8-methoxy-9-nitro-β-carboline (460 mg, 1.66 mmol) in EtOH (25 ml) was treated with $SnCl_2 \cdot 2H_2O$ (450 mg, 2.00 mmol). The reaction was stirred for 5 h at 65° C. and then concentrated. The crude product was chromatographed on silica eluting with a 5 to 10% methanol in chloroform gradient to provide 410 mg of 7-chloro-8-methoxy-9-nitro-β-carboline.

A solution of 7-chloro-8-methoxy-9-nitro-β-carboline (21 mg, 0.085 mmol) in pyridine (1 ml) was treated with nicotinyl chloride hydrochloride (54 mg, 0.30 mmol) and 4-dimethylaminopyridine (5 mg). After stirring at 95° C.–100° C. for 7 h the reaction was concentrated, the residue slurried with 10% $Na_2CO_3$, and then chromatographed on silica eluting with a 5% to 10% methanol in chloroform gradient to provide 4.7 mg of the title compound.

EXAMPLE 82

N-(6-Chloro-9H-β-carbolin-8-yl)-3,4-difluoro-benzamide

To a cold (3° C.–5° C.) solution of 9-amino-7-chloro-β-carboline (2.50 g, 11.5 mmol, as prepared in example 60 above) in pyridine (130 ml) was added 3,4-diflourobenzoyl chloride (1.67 ml, 13.25 mmol). The reaction was allowed to warm to RT and stirred for 20 h before diluting the reaction with water (60 ml) and 1M NaOH (15 ml). After stirring for 3 h at RT, the pH of the mixture was adjusted to 8–9 with 1M HCl and then poured into water (250 ml). The mixture was allowed to stand for 30 min and the product was filtered to provide 3.95 g of the title compound after washing with water and drying under reduced pressure at 55° C.–60° C.

EXAMPLE 83

6-Chloro-N-(6-chloro-9H-β-carbolin-8-yl)-nicotinamide

To a cold (3–5° C.) solution of 9-amino-7-chloro-β-carboline (1.40 g, 6.45 mmol, as prepared in example 60 above) in pyridine (72 ml) was added 6-chloro-nicotinyl chloride (1.30 g, 7.42 mmol). The reaction was allowed to warm to RT and stirred for 16 h before diluting the reaction with water (60 ml) and 1M NaOH (8 ml). After stirring for 40 min at RT, the mixture was poured into water (200 ml). The mixture was allowed to stand for 30 min and the product was filtered to provide 2.20 g of the title compound after washing with water and drying under reduced pressure at RT.

The examples in Table 1 show the structures of certain prepared compounds, including those of the previous examples, and were prepared according to methods used in the previous examples.

TABLE 1

| Example | Structure | Empirical formula | MS (M + H) |
|---|---|---|---|
| 1 | 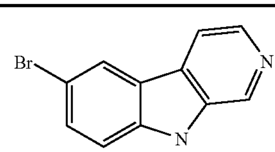 | $C_{11}H_7BrN_2$ | 248 |
| 2 | 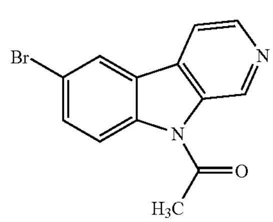 | $C_{13}H_9BrN_2O$ | 290 |
| 3 | 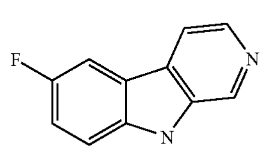 | $C_{11}H_7FN_2$ | 187 |

TABLE 1-continued

| Example | Structure | Empirical formula | MS (M + H) |
|---|---|---|---|
| 4 | (CH3)2CH-substituted β-carboline, CH | $C_{14}H_{15}ClN_2$ | 211 |
| 5 | 6-cyano-β-carboline | $C_{12}H_7N_3$ | 194 |
| 6 | 6-nitro-β-carboline, H—Cl | $C_{11}H_8ClN_3O_2$ | 214 |
| 7 | 6-(HO₂N)-β-carboline, trifluoroacetic acid | $C_{14}H_9F_3N_2O_4$ | 213 |
| 8 | 6,8-dibromo-β-carboline, ClH | $C_{11}H_7Br_2ClN_2$ | 327 |
| 9 | 6,8-dichloro-β-carboline | $C_{11}H_6Cl_2N_2$ | 238 |
| 10 | 6-bromo-9-(methylsulfonyl)-β-carboline | $C_{12}H_9BrN_2O_2S$ | 326 |
| 11 | 6-bromo-9-methyl-β-carboline | $C_{12}H_9BrN_2$ | 262 |

TABLE 1-continued

| Example | Structure | Empirical formula | MS (M + H) |
|---|---|---|---|
| 12 | 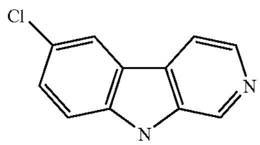 | $C_{11}H_7ClN_2$ | 204 |
| 13 | 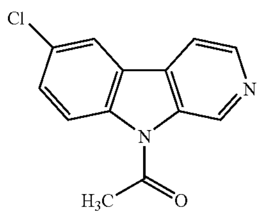 | $C_{13}H_9ClN_2O$ | 246 |
| 14 | 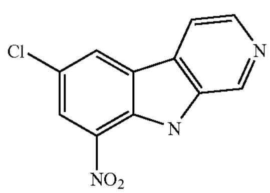 | $C_{11}H_6ClN_3O_2$ | 249 |
| 15 | 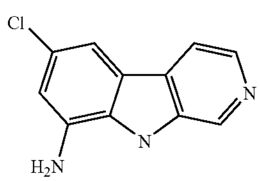 | $C_{11}H_8ClN_3$ | 219 |
| 16 | 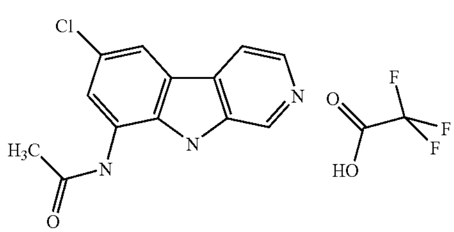 | $C_{16}H_{11}ClF_3N_3O_3$ | 261 |
| 17 | 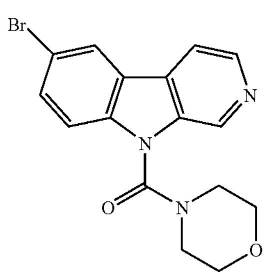 | $C_{16}H_{14}BrN_3O_2$ | 361 |
| 18 | 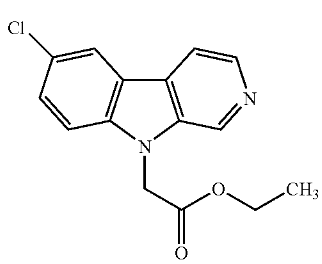 | $C_{15}H_{13}ClN_2O_2$ | 290 |

TABLE 1-continued
| Example | Structure | Empirical formula | MS (M + H) |
|---|---|---|---|
| 19 | 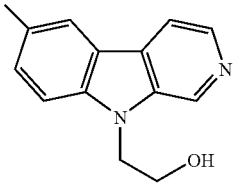 | $C_{13}H_{11}ClN_2O$ | 248 |
| 20 | 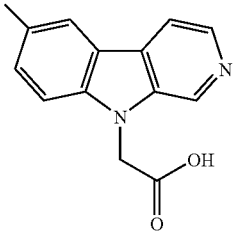 | $C_{13}H_9ClN_2O_2$ | 262 |
| 21 | 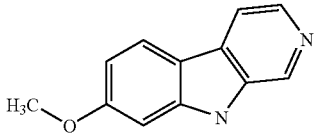 | $C_{12}H_{10}N_2O$ | 199 |
| 22 | 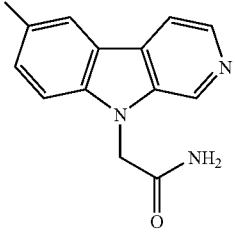 | $C_{13}H_{10}ClN_3O$ | 261 |
| 23 | 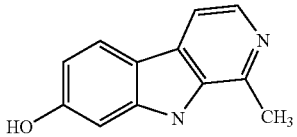 | $C_{12}H_{10}N_2O$ | 199 |
| 24 | 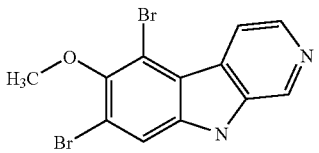 | $C_{12}H_8Br_2N_2O$ | 257 |
| 25 | 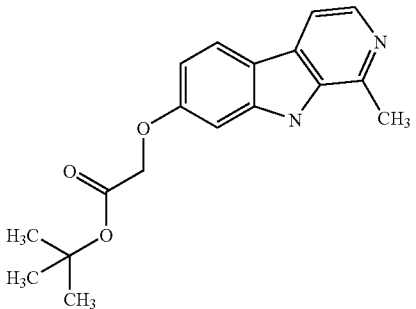 | $C_{18}H_{20}N_2O_3$ | 313 |

TABLE 1-continued

| Example | Structure | Empirical formula | MS (M + H) |
|---------|-----------|-------------------|------------|
| 26 | 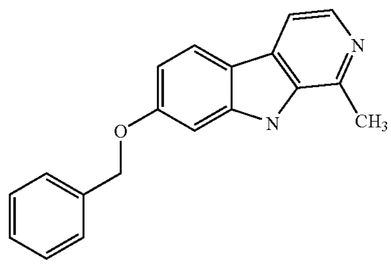 | C₁₉H₁₆N₂O | 289 |
| 27 | 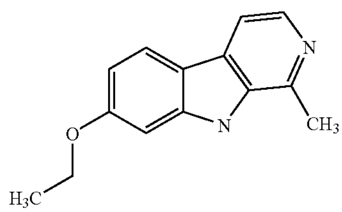 | C₁₄H₁₄N₂O | 227 |
| 28 | 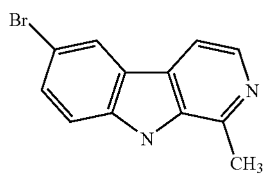 | C₁₂H₉BrN₂ | 262 |
| 29 | 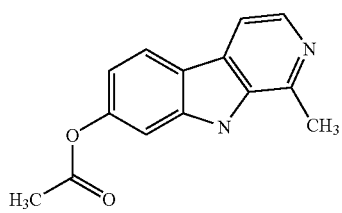 | C₁₄H₁₂N₂O₂ | 241 |
| 30 | 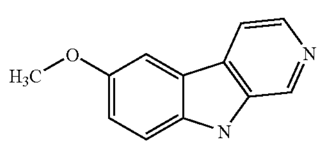 | C₁₂H₁₀N₂O | 199 |
| 31 | 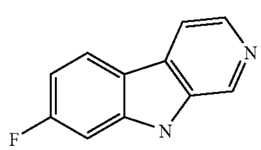 | C₁₁H₇FN₂ | 187 |
| 32 | 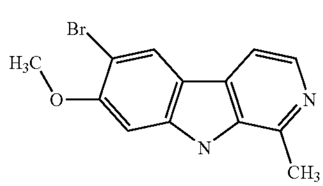 | C₁₃H₁₁BrN₂O | 292 |
| 33 | 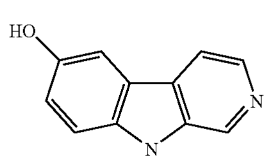 | C₁₁H₈N₂O | 185 |

TABLE 1-continued

| Example | Structure | Empirical formula | MS (M + H) |
|---|---|---|---|
| 34 | 6-chloro-7-fluoro-β-carboline | C₁₁H₆ClFN₂ | 222 |
| 35 | 6-methoxy-9-methyl-β-carboline | C₁₃H₁₂N₂O | 213 |
| 36 | 8-chloro-7-methoxy-β-carboline, trifluoroacetic acid | | 348 |
| 37 | 6,8-dichloro-7-methoxy-β-carboline, trifluoroacetic acid | | 382 |
| 38 | 6,8-dichloro-7-hydroxy-β-carboline | | 254 |
| 39 | 6,8-dichloro-7-ethoxy-β-carboline | | 282 |
| 40 | 6-chloro-7-fluoro-β-carboline | | 222 |
| 41 | 6-trifluoromethyl-1-hydroxy-β-carboline | | 253 |

TABLE 1-continued

| Example | Structure | Empirical formula | MS (M + H) |
|---------|-----------|-------------------|------------|
| 42 | 6-(trifluoromethyl)-β-carboline pyrido derivative | | 237 |
| 43 | 6-chloro-8-(methylamino)-β-carboline · trifluoroacetic acid | | 347 |
| 44 | 6-chloro-8-(dimethylamino)-β-carboline · trifluoroacetic acid | | 361 |
| 45 | 6-chloro-8-(methanesulfonylamino)-β-carboline · trifluoroacetic acid | | 411 |
| 46 | 6-chloro-8-(propionylamino)-β-carboline · trifluoroacetic acid | | 389 |
| 47 | 6-chloro-8-(benzoylamino)-β-carboline · trifluoroacetic acid | | 437 |
| 48 | 6-chloro-8-(N-methylacetylamino)-β-carboline · trifluoroacetic acid | | 388 |

TABLE 1-continued

| Example | Structure | Empirical formula | MS (M + H) |
|---|---|---|---|
| 49 | 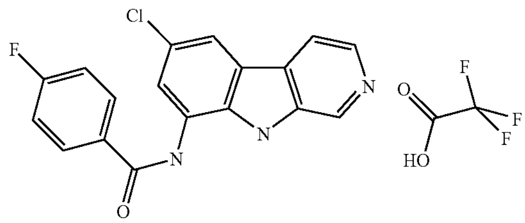 | | 454 |
| 50 | 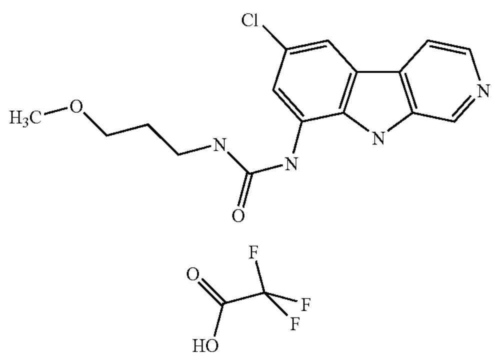 | | 448 |
| 51 | 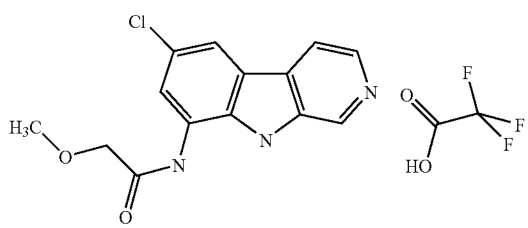 | | 404 |
| 52 | 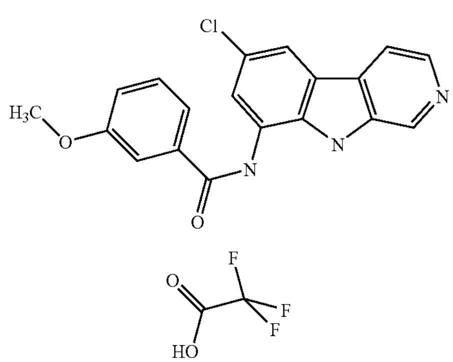 | | 467 |
| 53 | 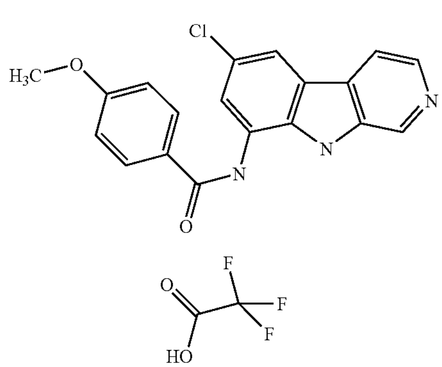 | | 467 |

TABLE 1-continued
| Example | Structure | Empirical formula | MS (M + H) |
|---|---|---|---|
| 54 | 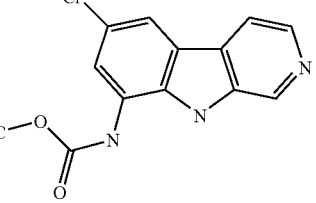 | | 391 |
| 55 | 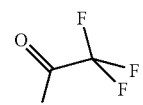 | | 416 |
| 56 | 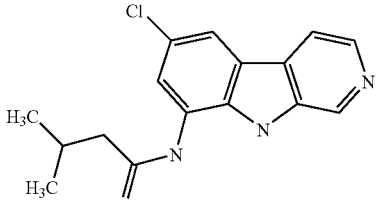 | $C_{19}H_{12}ClF_3N_4O_3$ | 323 |
| 57 | 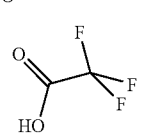 | $C_{18}H_{17}ClF_3N_3O_3$ | 302 |
| 58 | 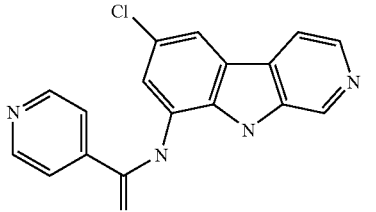 | $C_{16}H_{14}Cl_2N_2O_2$ | 338 |
| 59 | 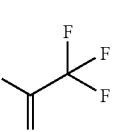 | $C_{16}H_{13}Cl_2N_3O_3$ | 367 |

TABLE 1-continued

| Example | Structure | Empirical formula | MS (M + H) |
|---|---|---|---|
| 60 | 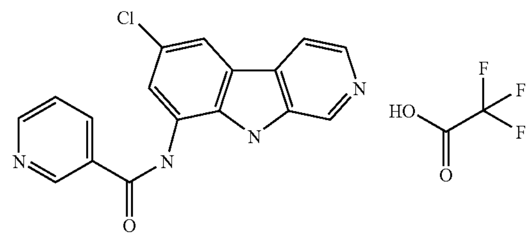 | C₁₉H₁₂ClF₃N₄O₃ | 323 |
| 61 | 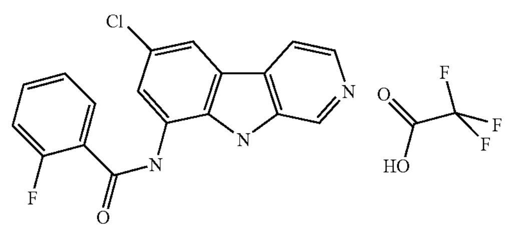 | C₂₀H₁₂ClF₄N₃O₃ | 340 |
| 62 | 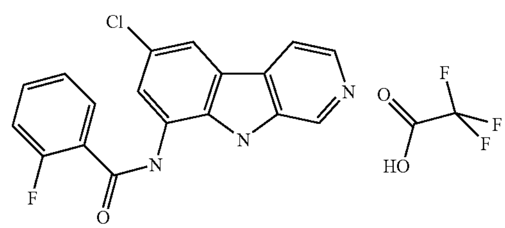 | C₂₀H₁₂ClF₄N₃O₃ | 340 |
| 63 | 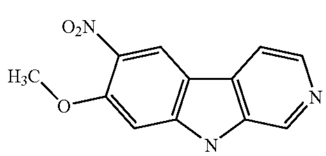 | C₁₂H₉N₃O₃ | 244 |
| 64 | 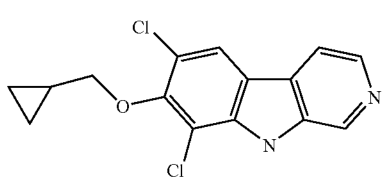 | C₁₅H₁₂Cl₂N₂O | 308 |
| 65 | 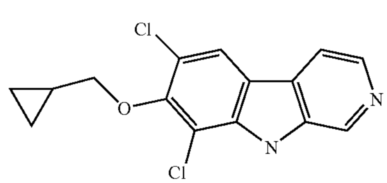 | C₁₅H₁₃Cl₃N₂O | |
| 66 | 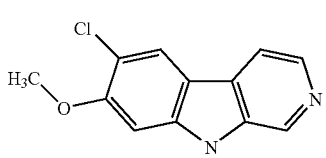 | C₁₂H₉ClN₂O | 234 |
| 67 | 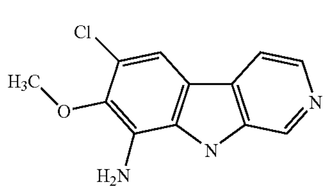 | C₁₂H₁₀ClN₃O | 249 |

TABLE 1-continued

| Example | Structure | Empirical formula | MS (M + H) |
|---|---|---|---|
| 68 | 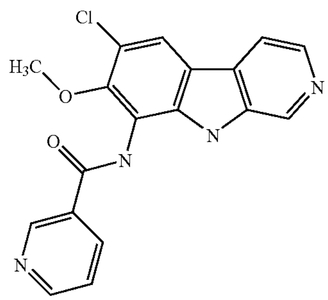 | $C_{18}H_{13}ClN_4O_2$ | 353 |
| 69 | 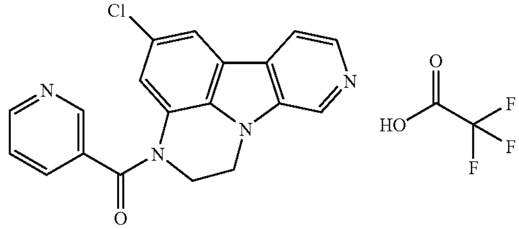 | $C_{21}H_{14}ClF_3N_4O_3$ | 349 |
| 70 | 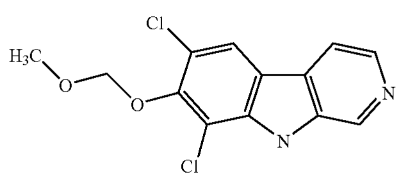 | $C_{13}H_{10}Cl_2N_2O_2$ | 298 |
| 71 | 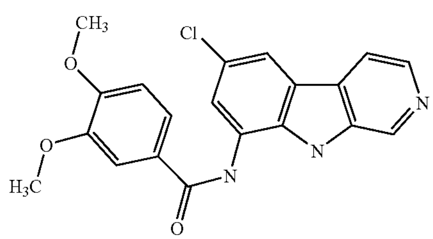 | $C_{20}H_{16}ClN_3O_3$ | 383 |
| 72 | 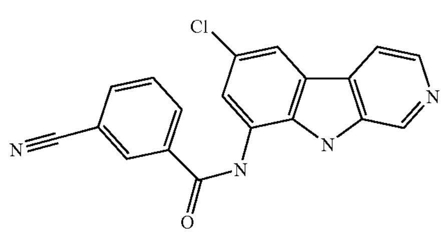 | $C_{19}H_{11}ClN_4O$ | 348 |
| 73 | 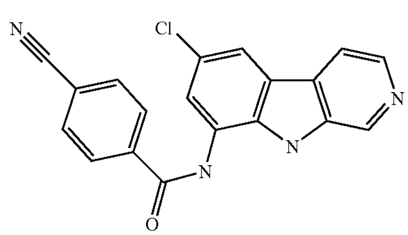 | $C_{19}H_{11}ClN_4O$ | 348 |

TABLE 1-continued

| Example | Structure | Empirical formula | MS (M + H) |
|---|---|---|---|
| 74 | 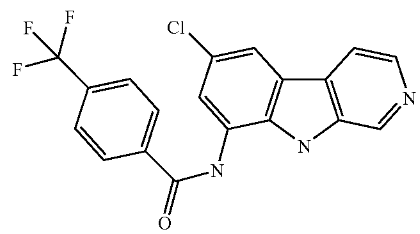 | $C_{19}H_{11}ClF_3N_3O$ | 391 |
| 75 | 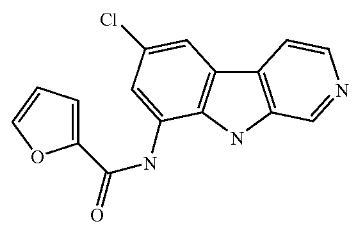 | $C_{16}H_{10}ClN_3O_2$ | 313 |
| 76 | 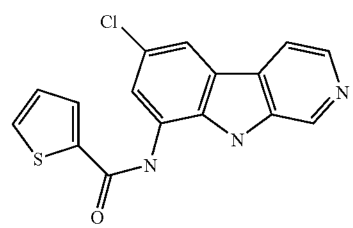 | $C_{16}H_{10}ClN_3OS$ | 329 |
| 77 | 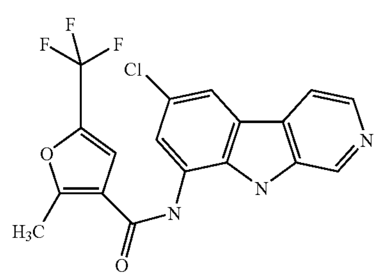 | $C_{18}H_{11}ClF_3N_3O_2$ | 395 |
| 78 | 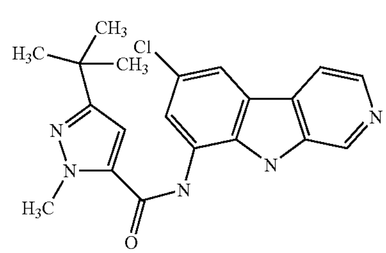 | $C_{20}H_{20}ClN_5O$ | 383 |
| 79 | 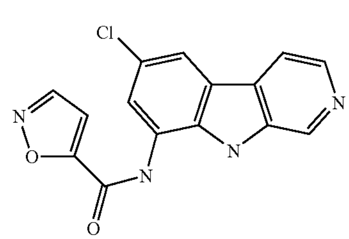 | $C_{15}H_9ClN_4O_2$ | 314 |

TABLE 1-continued

| Example | Structure | Empirical formula | MS (M + H) |
|---|---|---|---|
| 80 | 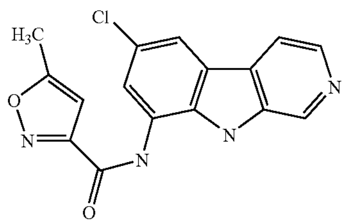 | $C_{16}H_{11}ClN_4O_2$ | 328 |
| 81 | 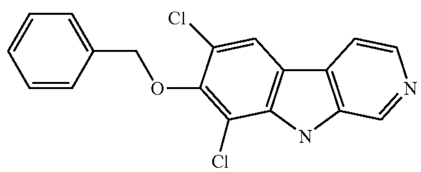 | $C_{18}H_{12}Cl_2N_2O$ | 344 |
| 82 | 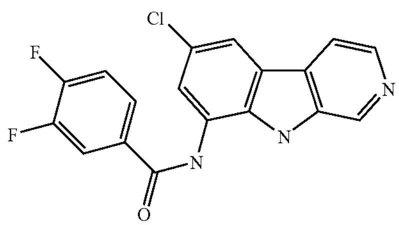 | $C_{18}H_{10}ClF_2N_3O$ | 359 |
| 83 | 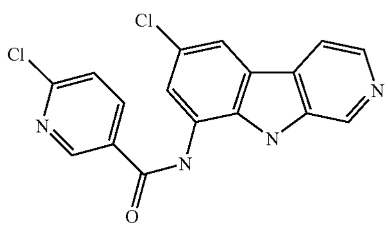 | $C_{17}H_{10}Cl_2N_4O$ | 358 |
| 84 | 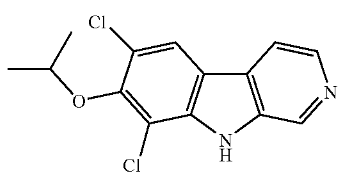 | $C_{14}H_{12}Cl_2N_2O$ | 296 |
| 85 | 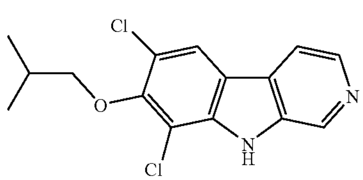 | $C_{15}H_{14}Cl_2N_2O$ | 310 |
| 86 | 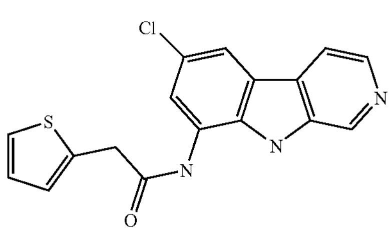 | $C_{17}H_{12}ClN_3OS$ | 343 |

TABLE 1-continued

| Example | Structure | Empirical formula | MS (M + H) |
|---------|-----------|-------------------|------------|
| 87 | 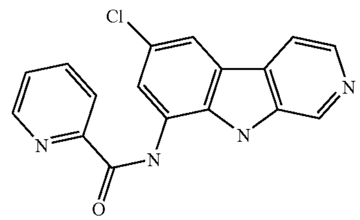 | $C_{17}H_{11}ClN_4O$ | 323 |
| 88 | 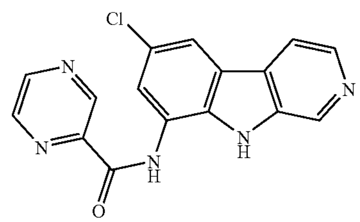 | $C_{16}H_{10}ClN_5O$ | 323 |
| 89 | 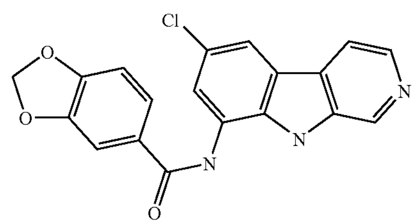 | $C_{19}H_{12}ClN_3O_3$ | 367 |
| 90 | 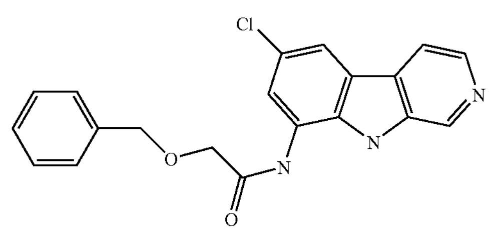 | $C_{20}H_{16}ClN_3O_2$ | 366 |
| 91 | 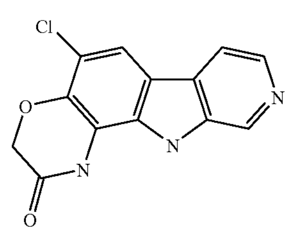 | $C_{13}H_8ClN_3O_2$ | 274 |
| 92 | 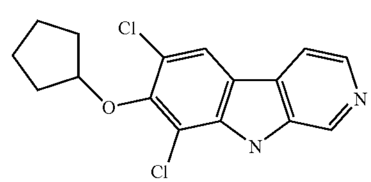 | $C_{16}H_{14}Cl_2N_2O$ | 322 |
| 93 | 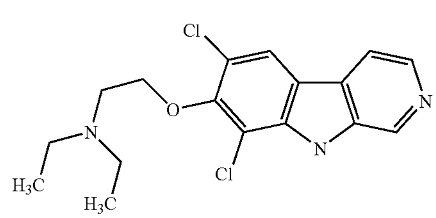 | $C_{17}H_{19}Cl_2N_3O$ | 353 |

TABLE 1-continued

| Example | Structure | Empirical formula | MS (M + H) |
|---|---|---|---|
| 94 | 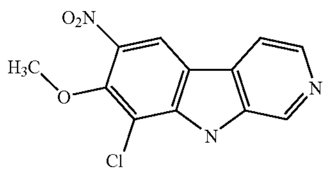 | $C_{12}H_8ClN_3O_3$ | 279 |
| 95 | 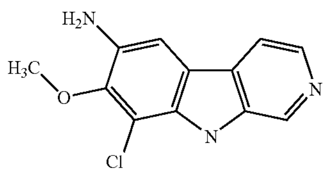 | $C_{12}H_{10}ClN_3O$ | 248 |
| 96 | 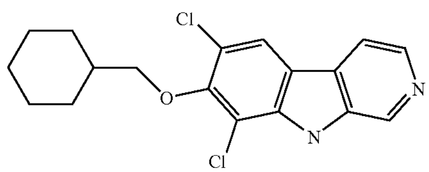 | $C_{18}H_{18}Cl_2N_2O$ | 350 |
| 97 | 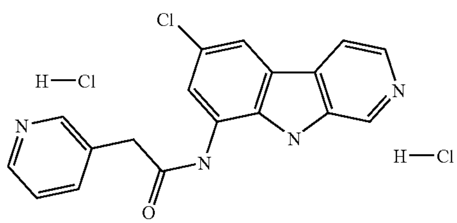 | $C_{18}H_{15}Cl_3N_4O$ | 337 |
| 98 | 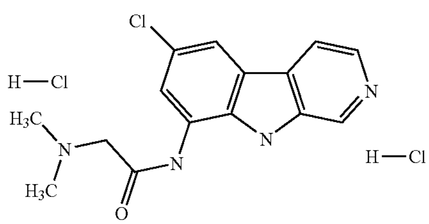 | $C_{15}H_{17}Cl_3N_4O$ | 290 |
| 99 | 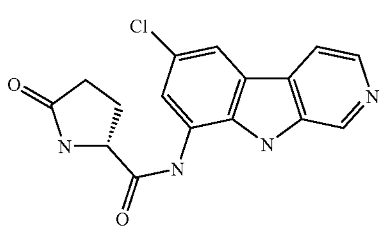 | $C_{16}H_{13}ClN_4O_2$ | 330 |
| 100 | 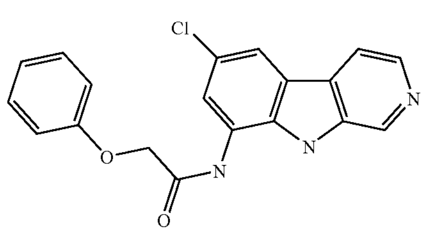 | $C_{19}H_{14}ClN_3O_2$ | 353 |

TABLE 1-continued

| Example | Structure | Empirical formula | MS (M + H) |
|---------|-----------|-------------------|------------|
| 101 | 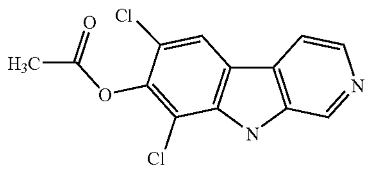 | C₁₃H₈Cl₂N₂O₂ | 296 |
| 102 | 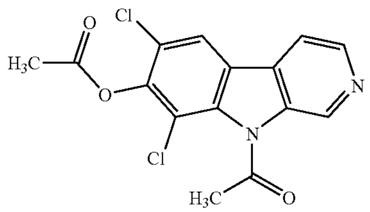 | C₁₅H₁₀Cl₂N₂O₃ | 338 |
| 103 | 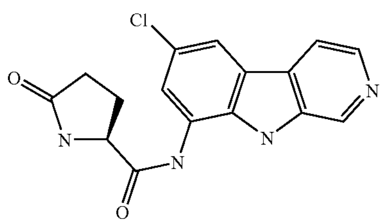 | C₁₆H₁₃ClN₄O₂ | 330 |
| 104 | 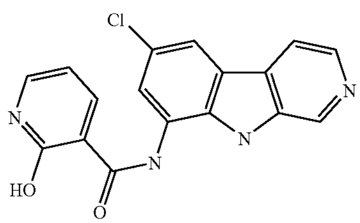 | C₁₇H₁₁ClN₄O₂ | 340 |
| 105 | 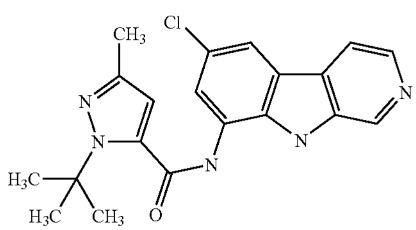 | C₂₀H₂₀ClN₅O | 383 |
| 106 | 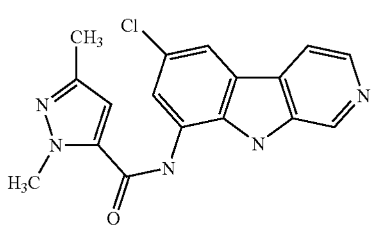 | C₁₇H₁₄ClN₅O | 341 |
| 107 | 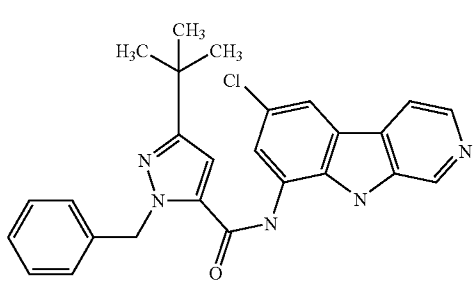 | C₂₆H₂₄ClN₅O | 359 |

TABLE 1-continued

| Example | Structure | Empirical formula | MS (M + H) |
|---|---|---|---|
| 108 | 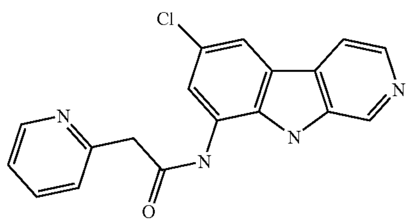 | $C_{18}H_{13}ClN_4O$ | 338 |
| 109 | 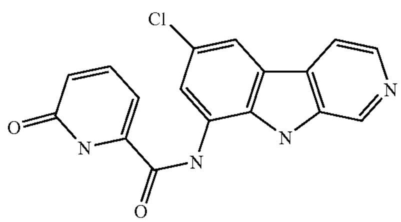 | $C_{17}H_{11}ClN_4O_2$ | 340 |
| 110 | 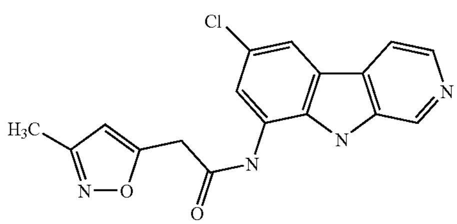 | $C_{17}H_{13}ClN_4O_2$ | 342 |
| 111 | 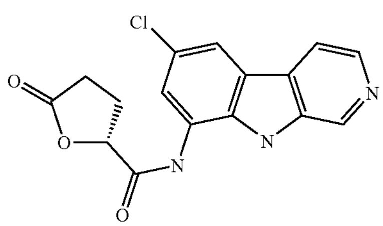 | $C_{16}H_{12}ClN_3O_3$ | 331 |
| 112 | 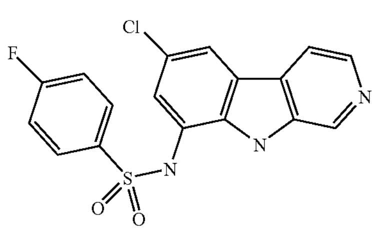 | $C_{17}H_{11}ClFN_3O_2S$ | 377 |
| 113 | 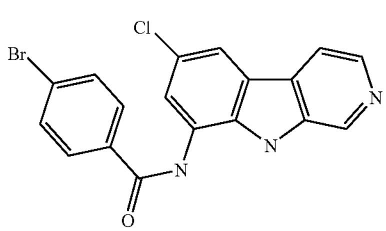 | $C_{18}H_{11}BrClN_3O$ | 401 |

TABLE 1-continued

| Example | Structure | Empirical formula | MS (M + H) |
|---|---|---|---|
| 114 | 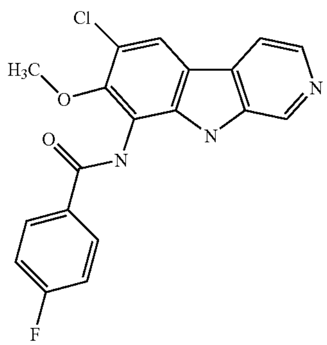 | $C_{19}H_{13}ClFN_3O_2$ | 371 |
| 115 | 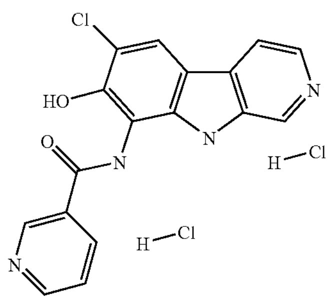 | $C_{17}H_{13}Cl_3N_4O_2$ | 339 |
| 116 | 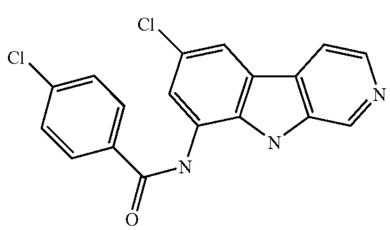 | $C_{18}H_{11}Cl_2N_3O$ | 357 |
| 117 | 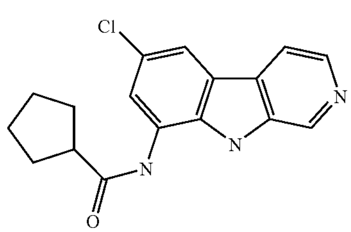 | $C_{17}H_{16}ClN_3O$ | 314 |
| 118 | 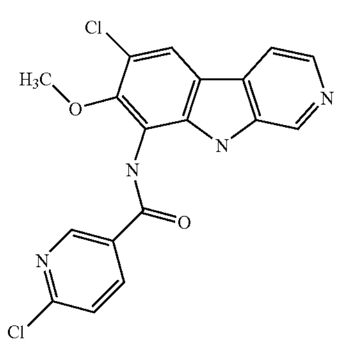 | $C_{18}H_{12}Cl_2N_4O_2$ | 388 |

TABLE 1-continued

| Example | Structure | Empirical formula | MS (M + H) |
|---|---|---|---|
| 119 | 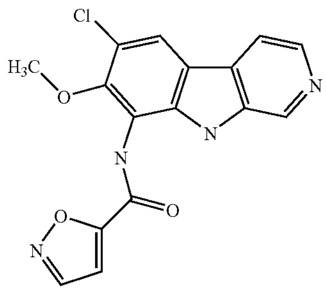 | $C_{16}H_{11}ClN_4O_3$ | 343 |
| 120 | 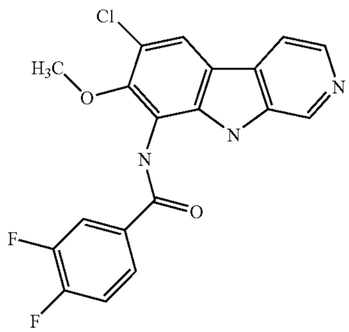 | $C_{19}H_{12}ClF_2N_3O_2$ | 390 |
| 121 | 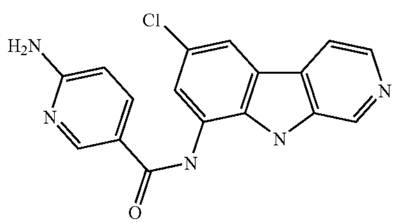 | $C_{17}H_{12}ClN_5O$ | 339 |

PHARMACOLOGICAL EXAMPLES $I_kB$-kinase ELISA

The in-vitro assay for detecting and measuring inhibition activity against IkBα-kinase complex by candidate pharmacological agents employs a biotinylated polypeptide spanning both Ser$^{32}$ and Ser$^{36}$ of IkBα and a specific antibody binding only to the phosphorylated form of the polypeptide, being either monoclonal or polyclonal (such as the commercially-available anti-phospho-serine$^{32}$ IkBα antibodies from New England Biolabs, Beverly, Mass., USA, cat. #9240). Once the antibody-phospho-polypeptide complex is formed, the complex can be detected by a variety of analytical methods utilizing such as radioactivity, luminescence, fluorescence or optical absorbance. For the use of the ELISA method, the complex can be immobilized either onto a biotin-binding plate (such as Neutravidin coated plate) and detected with a secondary antibody conjugated to HRP, or onto an antibody-binding plate (such as Protein-A coated plate) and detected With biotin-binding protein conjugated to HRP (such as Streptavidin-HRP). The level of activity can be correlated with a standard curve using synthetic phosphopeptides corresponding to the substrate polypeptide.

Experimental

IkBα kinase complex was prepared by first diluting 10 mL of HeLa S3 cell-extracts S100 fraction with 40 mL of 50 mM HEPES pH 7.5. Then, 40% ammonium sulfate was added and incubated on ice for 30 minutes. Precipitated pellet was redissolved with 5 mL of SEC buffer (50 mM HEPES pH 7.5, 1 mM DTT, 0.5 mM EDTA, 10 mM 2-glycerophosphate), clarified by centrifugation at 20,000×g for 15 min., and filtration through a 0.22 μm filter unit. Sample was loaded onto a 320-mL Superose-6 FPLC column (Amersham Pharmacia Biotech AB, Uppsala, Sweden) equilibrated with SEC buffer operated at 2 mL/min flow rate at 4° C. Fractions spanning the 670-kDa molecular-weight marker were pooled for activation. Kinase-containing pool was then activated by incubating with 100 nM MEKK1Δ, 250 μM MgATP, 10 mM MgCl$_2$, 5 mM DTT, 10 mM 2-glycerophosphate, 2.5 μM Microcystin-LR, for 45 minutes at 37° C. Activated enzyme was stored at 80° C. until further use. Per well of a 96-well plate, compounds at various concentrations in 2 μL DMSO were pre-incubated for 30 minutes at 25° C. with 43 μL of activated enzyme diluted [1:25] with assay buffer (50 mM HEPES pH 7.5, 5 mM DTT, 10 mM MgCl$_2$, 10 mM 2-glycerophosphate, 2.5 μM Microcystin-LR). Five microliters of peptide substrate (biotin-(CH$_2$)$_6$-DRHDSGLDSMKD-CONH$_2$) at 200 μM stock solution was added to each well and incubated for 1 hour before quenching with 150 μL of 50 mM HEPES pH 7.5, 0.1% BSA, 50 mM EDTA, plus [1:200] antibody. Quenched kinase reaction samples and phospho-peptide-calibration standards (biotin-(CH$_2$)$_6$-DRHDS[PO$_3$]GLDSMKD- CONH$_2$, serially diluted in assay buffer) at 100 µL per well were transferred to a Protein-A plate (Pierce Chemical Co., Rockford, Ill., USA) and incubated for 2 hours. with shaking. Following 3 washes with PBS, 100 µL of 0.5 µg/mL Streptavidin conjugated with HRP (horseradish peroxidase) diluted with 50 mM HEPES/0.1% BSA, was added for 30 minutes. After 5 washes with PBS, 100 µL TMB substrate (Kirkegaard & Perry Laboratories, Gaithersburg, Md., USA) was added and color development was stopped by adding 100 µL of 0.18 M H$_2$SO$_4$. Absorbance signals were recorded at 450 nm. Calibration-curve standards were fitted by linear regression using a 4-parameter dose-response equation. Based on this standard curve, levels of kinase activity were calculated in order to determine inhibition activity of candidate pharmacological agents.

Table 2 which follows shows the results.

TABLE 2

Kinase inhibition at a substance concentration of IC$_{50}$ in µM

| Example number | IkB-kinase IC$_{50}$ |
|---|---|
| 1 | 0.4 |
| 2 | 0.4 |
| 3 | 1 |
| 4 | 2.5 |
| 5 | 1 |
| 6 | 3 |
| 7 | 65 |
| 8 | 0.2 |
| 9 | 0.2 |
| 10 | 0.4 |
| 11 | 0.7 |
| 12 | 0.4 |
| 13 | 0.5 |
| 14 | 4 |
| 15 | 0.8 |
| 16 | 0.3 |
| 17 | 5 |
| 18 | 23 |
| 19 | 3 |
| 20 | 14 |
| 21 | 1.8 |
| 22 | 15 |
| 23 | 22 |
| 24 | 4.6 |
| 25 | 31 |
| 26 | 12 |
| 27 | 4.5 |
| 28 | 11 |
| 29 | 40 |
| 30 | 5.2 |
| 31 | 3.3 |
| 32 | 4.6 |
| 33 | 1.5 |
| 34 | 1 |
| 35 | 3.5 |
| 36 | 1.4 |
| 37 | 0.15 |
| 38 | 11 |
| 39 | 0.1 |
| 40 | 2 |
| 41 | 2.2 |
| 42 | 0.8 |
| 43 | 1 |
| 44 | 2 |
| 45 | 8.3 |
| 46 | 0.3 |
| 47 | 0.6 |
| 48 | 4 |
| 49 | 0.22 |
| 50 | 10 |
| 51 | 0.6 |
| 52 | 0.6 |
| 53 | 1.4 |
| 54 | 0.7 |
| 55 | 0.8 |
| 56 | 0.27 |
| 57 | 4.3 |
| 58 | 0.33 |
| 59 | 3.2 |
| 60 | 0.052 |
| 61 | 0.94 |
| 62 | 0.38 |
| 63 | 1.3 |
| 64 | 0.11 |
| 65 | 0.10 |
| 66 | 0.7 |
| 67 | 0.5 |
| 68 | 0.16 |
| 69 | 3.0 |
| 70 | 0.36 |
| 71 | 3.0 |
| 72 | 0.58 |
| 73 | 0.4 |
| 74 | 3.8 |
| 75 | 0.29 |
| 76 | 0.9 |
| 77 | 4.4 |
| 78 | 2.3 |
| 79 | 0.18 |
| 80 | 0.31 |
| 81 | 0.25 |
| 82 | 0.15 |
| 83 | 0.06 |
| 84 | 0.1 |
| 85 | 0.2 |
| 86 | 0.7 |
| 87 | 0.75 |
| 88 | 0.28 |
| 89 | 0.57 |
| 90 | 1.4 |
| 91 | 2.3 |
| 92 | 0.4 |
| 93 | 1.3 |
| 94 | 0.64 |
| 95 | 1.0 |
| 96 | 1.3 |
| 97 | 0.69 |
| 98 | 0.9 |
| 99 | 0.09 |
| 100 | 1.5 |
| 101 | 1.8 |
| 102 | 0.8 |
| 103 | 0.31 |
| 104 | 1.0 |
| 105 | 0.4 |
| 106 | 0.6 |
| 107 | 0.4 |
| 108 | 2.1 |
| 109 | 2.1 |
| 110 | 0.3 |
| 111 | 0.54 |
| 112 | 0.93 |
| 113 | 0.64 |
| 114 | 2.1 |
| 115 | 4.6 |
| 116 | 1.8 |
| 117 | 0.67 |
| 118 | 0.12 |
| 119 | 0.6 |
| 120 | 0.4 |

The compound according to example 121 shows a IC$_{50}$ of 1.7.

Mouse Heterotopic Cardiac Transplant Model

In the mouse heterotopic cardiac transplant model across full histocmpatibility barriers (BALB/c->C57BL/6 or B6/129), graft survival is typically limited to 7.3±0.4 days (mean±SD, n0 allografts) (see for example in Hancock W W, Sayegh M H, Zheng X G, Peach R, Linsley P S, Turka L A. Costimulatory function and expression of CD40-ligand, CD80 and CD86 or in vascularized murine cardiac allograft rejection. Proc Natl Acad Sci (USA) 93, 1996, 13967–13972; and Hancock W W, Buelow R, Sayegh M H, Turka L A. Antibody-induced transplant arteriosclerosis is prevented by graft expression of anti-oxidant and anti-apoptotic genes. Nature Med 4, 1998, 1392–1396).

The effects of oral administration of the compounds according to examples 49 and 60 were tested using 25 mg/kg/day for 14 days, starting at transplantation in said animal model. Whereas grafts in animals receiving the carrier, methyl-cellulose, rejected by 7 days (6.7±0.8), grafts in compound 49-treated mice survived around 15 days (15.3±0.6), and grafts in those given compound 60 survived for 20 days (20±1). Current immunosuppressive therapies used in transplantation have limited efficacy and/or considerable toxicity. Targeting of IkB-kinase with these agents significantly prolonged allograft survival without associated toxicity.

What is claimed is:

1. A compound of formula I

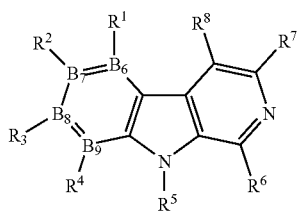

(I)

or a stereoisomeric form of a compound of formula I or a physiologically tolerable salt of a compound of formula I, wherein $B_6$, $B_7$, $B_8$ and $B_9$ are ring atoms independently chosen from carbon atoms and nitrogen atoms and wherein $B_6$, $B_7$, $B_8$ and $B_9$ together are no more than two nitrogen atoms at the same time;

where the substituents $R^1$, $R^2$, $R^3$, $R^4$ and $R^8$ may be independently chosen from
1. hydrogen atom,
2. halogen,
3. —OH,
4. —ON,
5. sulfo,
6. —NO$_2$,
7. —NH$_2$,
8. alkoxy,
9. substituted amino,
10. —NH—C(O)—R$^{15}$, wherein R$^{15}$ is a heterocycle having 5 to 7 ring atoms, an alkyl, an aryl, a substituted aryl or a substituted alkyl,
11. —COOH,
12. —O—R$^{10}$, wherein R$^{10}$ is alkyl, substituted alkyl or aryl,
13. —C(O)—R$^{12}$, wherein R$^{12}$ is alkyl, substituted alkyl or aryl,
14. —C(O)—O—R$^{12}$, wherein R$^{12}$ is alkyl, substituted alkyl or aryl,
15. aryl,
16. —O-aryl,
17. substituted aryl,
18. —O-substituted aryl,
19. alkyl,
20. substituted alkyl,
21. —CF$_3$ or
22. —CF$_2$—CF$_3$, provided that at least one of R$^1$, R$^2$, R$^3$, R$^4$ and R$^8$ is not a hydrogen atom, and provided that at least one of R$^1$, R$^3$, R$^4$ and R$^8$ is chosen from —NH—C(O)—R$^{15}$, wherein R$^{15}$ is an aryl or a substituted aryl;

R$^5$ is
1. hydrogen atom,
2. alkyl,
3. alkyl radical, substituted at one or more positions by one or more of the radicals, halogen, amino or hydroxyl,
4. —C(O)—R$^9$ or
5. —S(O)$_2$—R$^9$, in which
   R$^9$ is
   a) alkyl,
   b) alkyl radical, substituted at one or more positions by one or more of the radicals, halogen, amino or hydroxyl,
   c) aryl,
   d) aryl radical, substituted at one or more positions by one or more of the radicals, halogen, amino, or hydroxyl,
   e) —NH$_2$,
   f) alkoxy or
   g) substituted amino, and R$^6$ and R$^7$ may be independently chosen from
1. hydrogen atom,
2. halogen,
3. —OH,
4. methyl,
5. —O—(C$_1$–C$_{10}$)-alkyl, wherein alkyl is unsubstituted or mono- to tri- substituted by substituents independently chosen from
   5.1 aryl,
   5.2 halogen,
   5.3 —NO$_2$,
   5.4 sulfo,
   5.5 —COOH,
   5.6 —NH$_2$,
   5.7 —O—(C$_1$–C$_4$)-alkyl or
   5.8 —OH, or
6. —N(R$^{13}$)$_2$, wherein R$^{13}$ is independently of one another chosen from hydrogen atom, aryl, —C(O)—(C$_1$–C$_4$)-alkyl or substituted aryl or alkyl, wherein said —C(O)—(C$_1$–C$_4$)-alkyl is unsubstituted or mono- or tri- substituted independently of one another as defined under 5.1 to 5.8, or
R$^{13}$ together with the nitrogen atom to which it is bonded form a heterocycle having 5 to 7 ring atoms.

2. A compound of formula I as claimed in claim 1, or a physiologically tolerable salt of a compound of formula I, wherein
$B_6$, $B_7$, $B_8$, and $B_9$ are each a carbon atom,
R$^1$, R$^2$, R$^3$, R$^4$ and R$^8$ are independently chosen from
1. hydrogen atom,
2. halogen,
3. —CN, 4. —COOH,
5. —NO$_2$,
6. —NH$_2$,
7. —O—(C$_1$–C$_{10}$)-alkyl, wherein alkyl is unsubstituted or mono- to penta-substituted by substituents independently chosen from
   7.1 phenyl, which is unsubstituted or mono- to penta-substituted by substituents independently chosen from halogen or O—(C$_1$–C$_4$)-alkyl,
   7.2 halogen,
   7.3 —NH$_2$,
   7.4 —OH,
   7.5 —COOR$^{16}$, wherein R$^{16}$ is hydrogen atom or —(C$_1$–C$_{10}$)-alkyl,
   7.6 —NO$_2$,
   7.7 —S(O)$_y$—R$^{14}$, wherein y is zero, 1 or 2, R$^{14}$ is —(C$_1$–C$_{10}$)-alkyl, phenyl, amino, or N(R$^{13}$)$_2$, wherein the phenyl is unsubstituted or mono- to penta-substituted by substituents independently chosen from
      7.7.1 phenyi, which is unsubstituted or mono- to penta-substituted by substituents independently chosen from halogen or O—(C$_1$–C$_4$)-alkyl,
      7.7.2 halogen,
      7.7.3 —NH$_2$,
      7.7.4 —OH,
      7.7.5 —COOR$^{16}$, wherein R$^{16}$ is hydrogen atom or —(C$_1$–C$_{10}$)-alkyl,
      7.7.6 —NO$_2$,
      7.7.7 a radical selected from pyrrolidine, tetrahydropyridine, piperidine, piperazine, imidazoline, pyrazolidine, furan, morpholine, pyridine, pyridazine, pyrazine, oxolan, imidazoline, isoxazolidine, 2-isoxazoline, isothiazolidine, 2-isothiazoline, thiophene or thiomorpholine;
      7.7.8 —(C$_3$–C$_7$)-cycloalkyl;
      7.7.9 =O;
      7.7.10 —S(O)$_y$—R$^{14A}$, wherein y is as defined above in 7.7 and R$^{14A}$ is —(C$_1$–C$_{10}$)-alkyl, phenyl, amino, or N(R$^{13}$)$_2$, wherein the phenyl is unsubstituted or mono- to penta-substituted by substituents independently chosen from 7.7.1 to 7.7.9 or another —O-phenyl having its phenyl group either unsubstituted or substituted by substituents independently chosen from those as defined under 7.7.1 to 7.7.9, or
      7.7.11 —O-phenyl, wherein phenyl is unsubstituted or mono- to penta-substituted by substituents independently chosen from those as defined under 7.7.1 to 7.7.10 or another —O-phenyl having its phenyl group either unsubstituted or substituted by substituents independently chosen from those as defined under 7.7.1 to 7.7.10,
   and further wherein for the N(R$^{13}$)$_2$ substituent in paragraphs 7.7 and 7.7.10, R$^{13}$ is independently of one another chosen from hydrogen atom, phenyl, —(C$_1$–C$_{10}$)-alkyl, —C(O)—(C$_1$–C$_7$)-alkyl, —C(O)-phenyl, —C(O)—NH—(C$_1$–C$_7$)-alkyl, —C(O)—O-phenyl, —O(O)—NH-phenyl, —C(O)—O—(C$_1$–C$_7$)-alkyl, —S(O)$_y$—R$^{14A}$, wherein R$^{14A}$ and y are as defined above, and wherein the R$^{13}$ alkyl or phenyl groups in each case are unsubstituted or mono- to penta-substituted by substituents independently chosen from those as defined under 7.7.1 to 7.7.11, or R$^{13}$ together with the nitrogen atom to which it is bonded form a heterocycle having 5 to 7 ring atoms,
   7.8 —O-phenyl, wherein phenyl is unsubstituted or mono- to penta-substituted by substituents independently chosen from
      7.8.1 those as defined under 7.1 to 7.7,
      7.8.2 a radical selected from pyrrolidine, tetrahydropyridine, piperidine, piperazine, imidazoline, pyrazolidine, furan, morpholine, pyridine, pyridazine, pyrazine, oxolan, imidazoline, isoxazolidine, 2-isoxazoline, isothiazolidine, 2-isothiazoline, thiophene or thiomorpholine;
      7.8.3 —(C$_3$–C$_7$)-cycloalkyl
      7.8.4 =O
      7.8.5 —O-phenyl, wherein phenyl is unsubstituted or mono- to penta-substituted by substituents independently chosen from those as defined under 7.7.1 to 7.7.11,
   7.9 a radical selected from pyrrolidine, tetrahydropyridine, piperidine, piperazine, imidazoline, pyrazolidine, furan, morpholine, pyridine, pyridazine, pyrazine, oxolan, imidazoline, isoxazolidine, 2-isoxazoline, isothiazolidine, 2-isothiazoline, thiophene or thiomorpholine,
   7.10 —(C$_3$–C$_7$)-cycloalkyl or
   7.11 =O,
8. —N(R$^{13}$)$_2$, wherein R$^{13}$ is as defined in 7.7,
9. —NH—C(O)—R$^{15}$, wherein R$^{15}$ is
   9.1 a radical selected from pyrrolidine, tetrahydropyridine, piperidine, piperazine, imidazoline, pyrazolidine, furan, pyridazine, pyrazine, oxolan, imidazoline, isoxazolidine, 2-isoxazoline, isothiazolidine, 2-isothiazoline, thiophene or thiomorpholine,
   wherein said radical is unsubstituted or mono- to penta-substituted by substituents independently chosen from those as defined under 7.1 to 7.11, —CF$_3$, benzyl or by —(C$_1$–C$_{10}$)-alkyl, wherein alkyl is mono to tri-substituted independently of one another as defined under 7.1 to 7.11,
   9.2 —(C$_1$–C$_{10}$)-alkyl, wherein alkyl is unsubstituted or mono- to penta-substituted by substituents independently chosen from those as defined under 7.1 to 7.11 or by —O—(C$_1$–C$_{10}$)-alkyl, wherein alkyl is unsubstituted or mono- to penta-substituted by substituents independently chosen from those as defined under 7.1 to 7.11,
   9.3 —(C$_3$–C$_7$)-cycloalkyl,
   9.4 —N(R$^{13}$)$_2$, wherein R$^{13}$ is as defined in 7.7, or
   9.5 phenyl, wherein phenyl is unsubstituted or mono- to penta-substituted by substituents independently chosen from those as defined under 7.1 to 7.11, by —O—(C$_1$–C$_{10}$)-alkyl, by —CN, by —CF$_3$, by —(C$_1$–C$_{10}$)-alkyl,
   wherein alkyl is mono to tri-substituted by substituents independently chosen from those as defined under 7.1 to 7.11, or by two substituents of the phenyl radical which form a dioxolan ring,
   9.6 a radical selected from morpholine and pyridine wherein said radical is unsubstituted or mono- to penta-substituted by substituents independently chosen from those as defined under 7.1 to 7.11, —CF$_3$, benzyl or by —(C$_1$–C$_{10}$)-alkyl, wherein alkyl is unsubstituted or mono to tri-substituted independently of one another as defined under 7.1 to 7.11, 10. —S(O)y-R$^{14}$, wherein R$^{14}$ and y are as defined in 7.7,
11. —C(O)—R$^{12}$, wherein R$^{12}$ is phenyl or —(C$_1$–C$_7$)-alkyl, wherein phenyl or alkyl are unsubstituted or mono- to penta-substituted by substituents independently chosen from those as defined under 7.1 to 7.11,
12. —C(O)—O—R$^{12}$, wherein R$^{12}$ is phenyl or —(C$_1$–C$_7$)-alkyl, wherein phenyl or alkyl are unsubstituted or mono- to penta-substituted by substituents independently chosen from those as defined under 7.1 to 7.11,
13. —(C$_1$–C$_{10}$)-alkyl, wherein alkyl is unsubstituted or mono- to penta-substituted by substituents independently chosen from those as defined under 7.1 to 7.11,
15. —O—(C$_1$–C$_4$)-alkyl-(C$_3$–C$_7$)-cycloalkyl,
16. —(C$_1$–C$_4$)-alkyl-N(R$^{13}$)$_2$, wherein R$^{13}$ is as defined in 7.7
17. —CF$_3$ or
18. —CF$_2$–CF$_3$, provided that at least one of R$^1$, R$^2$, R$^3$, R$^4$ and R$^8$ is not a hydrogen atom, R$^5$ is
1. hydrogen atom,
2. —(C$_1$–C$_{10}$)-alkyl, wherein alkyl is unsubstituted or mono- to penta-substituted by substituents independently chosen from those as defined under 7.1 to 7.4,
3. —C(O)—R$^9$, wherein R$^9$ is
—NH$_2$, —(C$_1$–C$_{10}$)-alkyl, wherein alkyl is unsubstituted or mono- to penta-substituted by substituents independently chosen from those as defined under 7.1 to 7.4, or —N(R$^{13}$)$_2$, wherein R$^{13}$ is as defined in 7.7, or
4. —S(O)$_2$—R$^9$, wherein R$^9$ is as defined in 3 immediately above, or R$^4$ and R$^5$ together with the atom to which they are bonded form a heterocycle, or R$^3$ and R$^5$ together with the atom to which they are bonded form a heterocycle containing an additional oxygen atom in the ring and R$^6$ and R$^7$ independently of one another are chosen from hydrogen atom or methyl.

3. A compound as claimed in claim 2, wherein

B$_6$, B$_7$, B$_8$, and B$_9$ are each a carbon atom,

R$^1$, R$^2$, R$^3$ and R$^4$ independently of one another are hydrogen atom, halogen, cyano, nitro, amino, —O—(C$_1$–C$_7$)-alkyl, phenyl, —O-phenyl, —CF$_2$–CF$_3$, —CF$_3$, N(R$^{13}$)$_2$, wherein R$^{13}$ is independently of one another chosen from hydrogen atom, —(C$_1$–C$_4$)-alkyl, phenyl, —C(O)-phenyl, —C(O)-pyridyl, —C(O)—NH-phenyl, —C(O)—O-phenyl, —C(O)—O—(C$_1$–C$_4$)-alkyl, —C(O)—(C$_1$–C$_7$)-alkyl or —(C$_1$–C$_{10}$)-alkyl, wherein alkyl, pyridyl or phenyl are unsubstituted or mono- to tri-substituted by substituents independently chosen from those as defined under 7.1 to 7.11, or R$^{13}$ together with nitrogen atom to which it is bonded form a heterocycle having 5 to 7 ring atoms,
—S(O)$_y$—R$^{14}$,
wherein y is zero, 1 or 2, and R$^{14}$ is —(C$_1$–C$_{10}$)-alkyl, phenyl, which phenyl is unsubstituted or mono- to penta-substituted as defined for substituents under 7.1 to 7.11, amino or —N(R$^{13}$)$_2$,
wherein R$^{13}$ is independently of one another chosen from hydrogen atom, —(C$_1$–C$_7$)-alkyl-C(O)—(C$_1$–C$_7$)-alkyl, —C(O)-phenyl, C(O)-pyridyl, —C(O)—NH—(C$_1$–C$_4$)-alkyl, —C(O)—O-phenyl, —C(O)—O—(C$_1$–C$_4$)-alkyl or —(C$_1$–C$_{10}$)-alkyl, wherein each alkyl is unsubstituted or mono- to tri-substituted independently of one another as defined under 7.1 to 7.11, or R$^{13}$ together with nitrogen atom to which it is bonded form a heterocycle having 5 to 7 ring atoms, or
—C(O)—O—R$^{12}$, wherein R$^{12}$ is phenyl or —(C$_1$–C$_7$)-alkyl, wherein said phenyl or alkyl are unsubstituted or mono- to penta-substituted by substituents independently chosen from those as defined under 7.1 to 7.11, R$^6$, R$^7$ and R$^8$ independently of one another are hydrogen atom, methyl, amino, —N(R$^{13}$)$_2$, wherein R$^{13}$ is independently of one another chosen from
hydrogen atom, —(C$_1$–C$_7$)-alkyl-C(O)—(C$_1$–C$_7$)-alkyl, —C(O)-phenyl, C(O)-pyridyl, —C(O)—NH—(C$_1$–C$_4$)-alkyl, —C(O)—O-phenyl, —C(O)—O—(C$_1$–C$_4$)-alkyl or —(C$_1$–C$_{10}$)-alkyl, wherein pyridyl, alkyl or phenyl are unsubstituted or mono- to tri-substituted independently of one another as defined under 7.1 to 7.11, or
R$^{13}$ together with nitrogen atom to which it is bonded form a heterocycle having 5 to 7 ring atoms, provided that at least one of R$^1$, R$^2$, R$^3$, R$^4$ and R$^8$ is not a hydrogen atom.

4. A process for the preparation of a compound of the formula I (I)

wherein B$_6$, B$_7$, B$_8$ and B$_9$ are ring atoms independently chosen from carbon atoms and nitrogen atoms and wherein B$_6$, B$_7$, B$_8$ and B$_9$ together are no more than two nitrogen atoms at the same time;

where the substituents R$^1$, R$^2$, R$^3$, R$^4$ and R$^8$ may be independently chosen from
1. hydrogen atom,
2. halogen,
3. —OH,
4. —CN,
5. sulfo,
6. —NO$_2$,
7. —NH$_2$,
8. alkoxy,
9. substituted amino,
10. —NH—C(O)—R$^{15}$, wherein R$^{15}$ is a heterocycle having 5 to 7 ring atoms, an alkyl, an aryl, a substituted aryl or a substituted alkyl,
11. —COOH,
12. —O—R$^{10}$, wherein R$^{10}$ is alkyl, substituted alkyl or aryl,
13. —C(O)—R$^{12}$, wherein R$^{12}$ is alkyl, substituted alkyl or aryl, 14. —C(O)—O—$R^{12}$, wherein $R^{12}$ is alkyl, substituted alkyl or aryl,
15. aryl,
16. —O-aryl,
17. substituted aryl,
18. —O-substituted aryl,
19. alkyl,
20. substituted alkyl,
21. —$CF_3$ or
22. —$CF_2$—$CF_3$, provided that at least one of $R^1$, $R^2$, $R^3$, $R^4$ and $R^8$ is not a hydrogen atom, and provided that at least one of $R^1$, $R^2$, $R^3$, $R^4$ and $R^8$ is chosen from —NH—C(O)—$R^{15}$, wherein $R^{15}$ is an aryl or a substituted aryl;

$R^5$ is
1. hydrogen atom,
2. alkyl
3. alkyl radical, substituted at one or more positions by one or more of the radicals, halogen, amino or hydroxyl,
4. —C(O)—$R^9$ or
5. —$S(O)_2$—$R^9$, in which
   $R^9$ is
   a) alkyl,
   b) alkyl radical, substituted at one or more positions by one or more of the radicals, halogen, amino or hydroxyl,
   c) aryl,
   d) aryl radical, substituted at one or more positions by one or more of the radicals, halogen, amino, or hydroxyl,
   e) —$NH_2$,
   f) alkoxy or
   g) substituted amino, and $R^6$ and $R^7$ may be independently chosen from
1. hydrogen atom,
2. halogen,
3. —OH,
4. methyl,
5. —O—($C_1$–$C_{10}$)-alkyl, wherein alkyl is unsubstituted or mono- to tri-substituted by substituents independently chosen from
   5.1 aryl,
   5.2 halogen,
   5.3 —$NO_2$,
   5.4 sulfo,
   5.5 —COOH,
   5.6 —$NH_2$,
   5.7 —O—($C_1$–$C_4$)-alkyl or
   5.8 —OH, or
6. —N($R^{13}$)$_2$, wherein $R^{13}$ is independently of one another chosen from hydrogen atom, aryl, —C(O)—($C_1$–$C_4$)-alkyl or substituted aryl or alkyl, wherein said —C(O)—($C_1$–$C_4$)-alkyl is unsubstituted or mono- or tri-substituted independently of one another as defined under 5.1 to 5.8, or $R^{13}$ together with the nitrogen atom to which it is bonded form a heterocycle having 5 to 7 ring atoms which comprises
reacting a compound of formula III

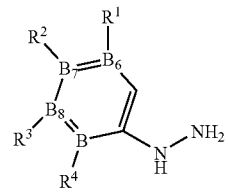

(III)

in which $R^1$, $R^2$, $R^3$, $R^4$, $B_6$, $B_7$, $B_8$ and $B_9$ are each as defined in formula I, with a compound of the formula IV,

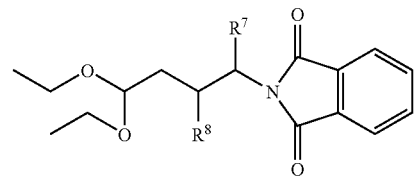

(IV)

in the presence of a acid, to yield a compound of the formula V

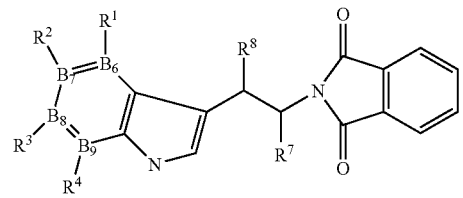

(V)

which is reacted with hydrazine hydrate and later with $R^6$CHO or formaldehyde ($R^6$ is H) to give a compound of formula VI

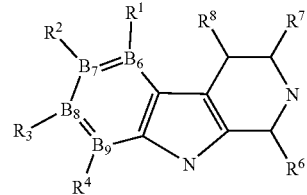

(VI)

and then oxidizing the compound of formula VI to give a compound of the formula VII,

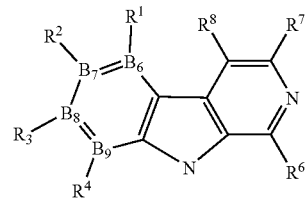

(VII)

where $R^1$ to $R^4$, $R^6$ to $R^8$ and $B_6$ to $B_9$ are as defined in formula I, to give a compound of formula I.

5. A process according to claim 4, wherein a compound of the formula VII is reacted with a compound of the formula VIII

 (VIII)

where Y is halogen or —OH and $R^5$ is as defined in formula I, to give a compound of the formula I.

6. A process according to claim 4, which further comprises resolving a compound of the formula I formed by the process of claim 4, which on account of its chemical structure occurs in enantiomeric forms, into the pure enantiomers by salt formation with enantiomerically pure acids or bases, chromatography on chiral stationary phases or derivatization by means of chiral enantiomerically pure compounds, separation of the diastereomers thus obtained, and removal of the chiral auxiliary groups.

7. The process according to claim 6, wherein the chiral enantiomerically pure compounds are amino acids.

8. A process according to claim 5, which further comprises resolving a compound of the formula I formed by the process of claim 5, which on account of its chemical structure occurs in enantiomeric forms, into the pure enantiomers by salt formation with enantiomerically pure acids or bases, chromatography on chiral stationary phases or derivatization by means of chiral enantiomerically pure, separation of the diastereomers thus obtained, and removal of the chiral auxiliary groups.

9. The process according to claim 8, wherein the chiral enantiomerically pure compounds are amino acids.

10. A process according to claim 4, which further comprises isolating a compound of the formula I prepared by the process of claim 4, either in free form or, in the case of the presence of acidic or basic groups, converting it into a physiologically tolerable salt.

11. A process according to claim 5, which further comprises isolating a compound of the formula I prepared by the process of claim 5, either in free form or, in the case of the presence of acidic or basic groups, converting it into a physiologically tolerable salt.

12. A process according to claim 6, which further comprises isolating a compound of the formula I prepared by the process of claim 6, either in free form or, in the case of the presence of acidic or basic groups, converting it into a physiologically tolerable salt.

13. A composition which comprises an efficacious amount of at least one compound chosen from the compounds of formula I

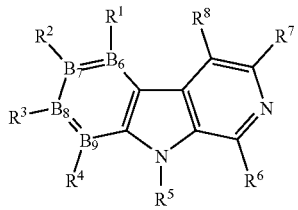 (I)

wherein $B_6$, $B_7$, $B_8$ and $B_9$ are ring atoms independently chosen from carbon atoms and nitrogen atoms and wherein $B_6$, $B_7$, $B_8$ and $B_9$ together are no more than two nitrogen atoms at the same time;

where the substituents $R^1$, $R^2$, $R^3$, $R^4$ and $R^8$ may be independently chosen from
1. hydrogen atom,
2. halogen,
3. —OH,
4. —CN,
5. sulfo,
6. —NO$_2$,
7. —NH$_2$,
8. alkoxy,
9. substituted amino,
10. —NH—C(O)—$R^{15}$, wherein $R^{15}$ is a heterocycle having 5 to 7 ring atoms, an alkyl, an aryl, a substituted aryl or a substituted alkyl,
11. —COOH,
12. —O—$R^{10}$, wherein $R^{10}$ is alkyl, substituted alkyl or aryl,
13. —C(O)—$R^{12}$, wherein $R^{12}$ is alkyl, substituted alkyl or aryl,
14. —C(O)—O—$R^{12}$, wherein $R^{12}$ is alkyl, substituted alkyl or aryl,
15. aryl,
16. —O-aryl,
17. substituted aryl,
18. —O-substituted aryl,
19. alkyl,
20. substituted alkyl,
21. —CF$_3$ or
22. —CF$_2$—CF$_3$, provided that at least one of $R^1$, $R^2$, $R^3$, $R^4$ and $R^8$ is not a hydrogen atom, and provided that at least one of $R^1$, $R^2$, $R^3$, $R^4$ and $R^8$ is chosen from —NH—C(O)—$R^{15}$, wherein $R^{15}$ is an aryl or a substituted aryl;

$R^5$ is
1. hydrogen atom,
2. alkyl,
3. alkyl radical, substituted at one or more positions by one or more of the radicals, halogen, amino or hydroxyl,
4. —C(O)—$R^9$ or
5. —S(O)$_2$—$R^9$, in which
   $R^9$ is
   a) alkyl,
   b) alkyl radical, substituted at one or more positions by one or more of the radicals, halogen, amino or hydroxyl,
   d) aryl radical, substituted at one or more positions by one or more of the radicals, halogen, amino, or hydroxyl,
   e) —NH$_2$,
   f) alkoxy or
   g) substituted amino, and $R^6$ and $R^7$ may be independently chosen from
1. hydrogen atom,
2. halogen,
3. —OH,
4. methyl,
5. —O—(C$_1$–C$_{10}$)-alkyl, wherein alkyl is unsubstituted or mono- to tri-substituted by substituents independently chosen from
   5.1 aryl,
   5.2 halogen,
   5.3 —NO$_2$,
   5.4 sulfo,
   5.5 —COOH,
   5.6 —NH$_2$,
   5.7 —O—(C$_1$–C$_4$)-alkyl or
   5.8 —OH, or
6. —N(R$^{13}$)$_2$, wherein $R^{13}$ is independently of one another chosen from hydrogen atom, aryl, —C(O)—(C$_1$–C$_4$)-alkyl or substituted aryl or alkyl, wherein said —C(O)—($C_1$–$C_4$)-alkyl is unsubstituted or mono- or tri-substituted independently of one another as defined under 5.1 to 5.8, or $R^{13}$ together with the nitrogen atom to which it is bonded form a heterocycle having 5 to 7 ring atoms a physiologically tolerable salt of the compounds of the formula I or an optionally stereoisomeric form of the compounds of the formula I, together with at least one pharmaceutically suitable and physiologically tolerable excipient, additive, active compound or auxiliary.

14. A method for treating a patient experiencing at least one disorder involving an increased activity of $I_\kappa B$ kinase where the disorder is atherosclerosis, the method comprising administering to the patient an efficacious amount of at least one compound chosen from a compound of formula I as set forth in claim 1, a stereoisomeric form of a compound of the formula I, or a physiologically tolerable salt of a compound of the formula I.

* * * * *

UNITED STATES PATENT AND TRADEMARK OFFICE
CERTIFICATE OF CORRECTION

PATENT NO. : 7,026,331 B2
APPLICATION NO. : 10/627978
DATED : April 11, 2006
INVENTOR(S) : Olaf Ritzeler et al.

It is certified that error appears in the above-identified patent and that said Letters Patent is hereby corrected as shown below:

On the Title Page, Item (54), and col. 1, line 1, in the Title, "BETA-CARBOLINES" should read --BETA CARBOLINES--.

In claim 1, column 73, line 54, "-ON," should read -- -CN,--.

In claim 1, column 74, line 9, "-$CF_3$or" should read -- -$CF_3$ or--.

In claim 1, column 74, line 10, "-$CF_2$-$CF_3$," should read-- -$CF_2$-$CF_3$,--.

In claim 2, column 75, line 5, "penta-substituted" should read --penta- substituted--.

In claim 2, column 75, line 8, "penta-substituted" should read --penta- substituted--.

In claim 2, column 75, line 19, "penta-substituted" should read --penta- substituted--.

In claim 2, column 75, line 21, "phenyi," should read --phenyl,--.

In claim 2, column 75, line 22, "penta-substituted" should read --penta- substituted--.

In claim 2, column 75, line 42, "penta-substituted" should read --penta- substituted--.

In claim 2, column 75, line 49, "penta-substituted" should read --penta- substituted--.

In claim 2, column 75, line 61, "-O(O)-NH-phenyl," should read -- -C(O)-NH-phenyl,--.

In claim 2, column 75, lines 65-66, "penta-substituted' should read --penta- substituted--.

In claim 2, column 76, line 5, "penta-substituted" should read --penta- substituted--.

In claim 2, column 76, line 17, "penta-substituted" should read --penta- substituted--.

UNITED STATES PATENT AND TRADEMARK OFFICE
CERTIFICATE OF CORRECTION

| | |
|---|---|
| PATENT NO. | : 7,026,331 B2 |
| APPLICATION NO. | : 10/627978 |
| DATED | : April 11, 2006 |
| INVENTOR(S) | : Olaf Ritzeler et al. |

It is certified that error appears in the above-identified patent and that said Letters Patent is hereby corrected as shown below:

In claim 2, column 76, line 37, "penta-substituted" should read --penta- substituted--.

In claim 2, column 76, line 40, "tri-substituted" should read --tri- substituted--.

In claim 2, column 76, line 43, "penta-substituted" should read --penta- substituted--.

In claim 2, column 76, lines 46-47, "penta-substituted" should read --penta- substituted--.

In claim 2, column 76, line 52, "penta-substituted" should read --penta- substituted--.

In claim 2, column 76, line 56, "tri-substituted" should read --tri- substituted--.

In claim 2, column 76, line 62, "penta-substituted" should read --penta- substituted--.

In claim 2, column 76, line 65, "tri-substituted" should read --tri- substituted--.

In claim 2, column 77, line 5, "penta-substituted" should read --penta- substituted--.

In claim 2, column 77, line 10, "penta-substituted" should read --penta- substituted--.

In claim 2, column 77, line 14, "penta-substituted" should read --penta- substituted—.

In claim 2, column 77, line 16, after "7.11,", insert the following line:

--14. -O-$(C_1$-$C_6)$-alkyl-O-$(C_1$-$C_6)$-alkyl,--.

In claim 2, column 77, line 17, "-O-$(C_1$-$C_4)$-alkyl-$(C_3$-$C_7)$-cycloalkyl," should read -- -O-$(C_0$-$C_4)$-alkyl-$(C_3$-$C_7)$-cycloalkyl,--.

UNITED STATES PATENT AND TRADEMARK OFFICE
CERTIFICATE OF CORRECTION

| | |
|---|---|
| PATENT NO. | : 7,026,331 B2 |
| APPLICATION NO. | : 10/627978 |
| DATED | : April 11, 2006 |
| INVENTOR(S) | : Olaf Ritzeler et al. |

It is certified that error appears in the above-identified patent and that said Letters Patent is hereby corrected as shown below:

In claim 2, column 77, line 20, "-$CF_3$or" should read -- -$CF_3$ or--.

In claim 2, column 77, line 24, "$R^5$is" should read --$R^5$ is--.

In claim 2, column 77, line 27, "penta-substituted" should read --penta- substituted--.

In claim 2, column 77, line 31, "penta-substituted" should read --penta- substituted--.

In claim 3, column 77, line 51, "-$(C_1$-$C_4)$-alkyl," should read -- -$(C_1$-$C_7)$-alkyl,--.

In claim 3, column 77, line 56, "tri-substituted" should read --tri- substituted--.

In claim 3, column 77, line 64, "penta-substituted" should read --penta- substituted--.

In claim 3, column 78, line 5, "tri-substituted" should read --tri- substituted--.

In claim 3, column 78, line 11, "penta-substituted" should read --penta- substituted--.

In claim 3, column 78, line 22, "tri-substituted" should read --tri- substituted--.

In claim 4, column 78, line 30, "formuia" should read --formula--.

In claim 4, column 78, line 62, "aryi" should read --aryl--.

In claim 4, column 79, line 18, "$R^5$is" should read --$R^5$ is--.

In claim 4, column 79, line 27, "$R^9$is" should read --$R^9$ is--.

In claim 4, column 79, line 48, "tri-substituted" should read --tri- substituted--.

UNITED STATES PATENT AND TRADEMARK OFFICE
CERTIFICATE OF CORRECTION

PATENT NO. : 7,026,331 B2
APPLICATION NO. : 10/627978
DATED : April 11, 2006
INVENTOR(S) : Olaf Ritzeler et al.

It is certified that error appears in the above-identified patent and that said Letters Patent is hereby corrected as shown below:

In claim 4, column 79, line 64, "tri-substituted" should read --tri- substituted--.

In claim 4, column 79, line 67, "ring atoms", should read --ring atoms,--.

In claim 4, column 80, lines 5-12, in the structure for formula (III):

"
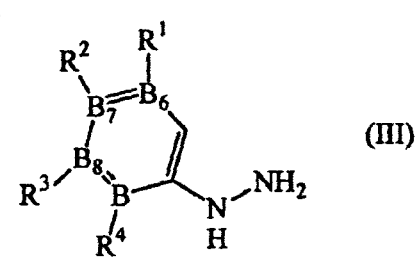
(III)
"

should read

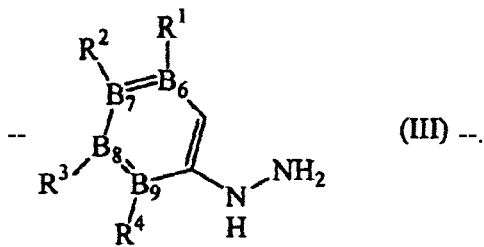
-- (III) --.

In claim 4, column 80, line 27, "a acid," should read --an acid,--.

In claim 13, column 82, line 42, after "hydroxyl", insert the line:

--c) aryl,--.

In claim 13, column 82, line 55, "tri-substituted" should read --tri- substituted--.

UNITED STATES PATENT AND TRADEMARK OFFICE
CERTIFICATE OF CORRECTION

| | |
|---|---|
| PATENT NO. | : 7,026,331 B2 |
| APPLICATION NO. | : 10/627978 |
| DATED | : April 11, 2006 |
| INVENTOR(S) | : Olaf Ritzeler et al. |

It is certified that error appears in the above-identified patent and that said Letters Patent is hereby corrected as shown below:

In claim 13, column 83, line 2, "tri-substituted" should read --tri- substituted--.

Signed and Sealed this

Seventeenth Day of October, 2006

JON W. DUDAS
*Director of the United States Patent and Trademark Office*